US008222204B2

(12) United States Patent
Garry et al.

(10) Patent No.: US 8,222,204 B2
(45) Date of Patent: Jul. 17, 2012

(54) INFLUENZA INHIBITING COMPOSITIONS AND METHODS

(75) Inventors: Robert F. Garry, New Orleans, LA (US); Russell B. Wilson, Mandeville, LA (US)

(73) Assignee: The Administrators of the Tulane Educational Fund and Autoimmune Technologies, LLC, New Orleans, LA (US)

( * ) Notice: Subject to any disclaimer, the term of this patent is extended or adjusted under 35 U.S.C. 154(b) by 177 days.

(21) Appl. No.: 12/378,561

(22) Filed: Feb. 17, 2009

(65) Prior Publication Data

US 2009/0234096 A1 Sep. 17, 2009

Related U.S. Application Data

(63) Continuation of application No. PCT/US2008/007918, filed on Jun. 25, 2008.

(60) Provisional application No. 60/937,120, filed on Jun. 25, 2007.

(51) Int. Cl.
*A61K 38/04* (2006.01)
*C07K 7/08* (2006.01)

(52) U.S. Cl. ........................................ 514/3.7; 530/326

(58) Field of Classification Search .................. None
See application file for complete search history.

(56) References Cited

U.S. PATENT DOCUMENTS

| | | | |
|---|---|---|---|
| 5,464,933 A | 11/1995 | Bolognesi et al. | |
| 5,567,805 A | 10/1996 | Henderson et al. | |
| 5,747,239 A | 5/1998 | Wang et al. | |
| 6,037,348 A | 3/2000 | Colacino et al. | |
| 6,068,973 A * | 5/2000 | Barney et al. | 435/5 |
| 7,420,028 B2 | 9/2008 | Bogoch et al. | |
| 7,442,761 B2 | 10/2008 | Bogoch et al. | |
| 7,452,963 B2 | 11/2008 | Bogoch et al. | |
| 7,674,880 B2 | 3/2010 | Bogoch et al. | |
| 7,705,129 B2 | 4/2010 | Bogoch et al. | |
| 7,758,863 B2 | 7/2010 | Bogoch et al. | |
| 7,763,705 B2 | 7/2010 | Bogoch et al. | |
| 7,774,144 B2 | 8/2010 | Bogoch et al. | |
| 7,894,999 B2 | 2/2011 | Bogoch et al. | |
| 2003/0180328 A1 | 9/2003 | Bagoch et al. | |
| 2007/0026009 A1 * | 2/2007 | Bogoch et al. | 424/186.1 |

FOREIGN PATENT DOCUMENTS

| | | | |
|---|---|---|---|
| WO | WO 88/08429 | | 11/1988 |
| WO | WO 94/17826 | * | 8/1994 |
| WO | 0032228 A2 | | 6/2000 |
| WO | WO 01/59457 A2 | | 8/2001 |
| WO | WO 2005/010034 A1 | | 2/2005 |
| WO | WO 2005/016238 A2 | | 2/2005 |
| WO | WO 2005/044992 | * | 5/2005 |

OTHER PUBLICATIONS

Cantin et al., Am. J. Respir. Cell Mol. Biol., 2002, 27:659-665.*
Roberts et al., Advanced Drug Delivery Reviews, 2002, 54:459-476.*
R.J. Russel et al., Structure of Influenza Hemagglutinin in Complex with an Inhibitor of Membrane Fusion, PNAS, vol. 105, No. 46, 17736-17741, (2008).
D. Fass et al., Dissection of a Retrovirus Envelope Protein Reveals Structural Similarity to Influenza Hemagglutinin, Current Biology, vol. 5, No. 12, 1377-1383, (1995).
C. M. Carr et al., A Spring-Loaded Mechanism for the Conformational Change of Influenza Hemagglutinin, Cell, vol. 73, pp. 823-832, (1993).
J.C.S. Clegg et al., Nucleotide Sequence of the S RNA of Lassa Virus . . . of Arenavirus Gene Products, Virus Research, 18 151-164 (1990).
D.C. Chan et al., Evidence that a Prominent Cavity in the Coiled Coil of HIV . . . Attractive Drug Target, Proc. Natl. Acad. Sci.,vol. 95, 15613-15617, (1998).
S. F. Atabani et al., Identification of an Immunodominant Neutralizing . . . Human Sera From Acute Infection; Journal of Virology, 7240-7245, (1997).
O. Samuel et al., Participation of Two Fusion Peptides in Measles Virus-Induced Membrane Fusion: . . . With Other Paramyxoviruses, Biochemistry 40, 1340-1349, (2001).
Y. Kliger et al., Cloaked Similarity Between HIV-1 and SARS-CoV Suggests an Anti-SARS Strategy, BMC Microbiology vol. 3, Research Article, 2003.
Gelder et al., "Human CD4+ T-Cell Repertoire of Responses to Influenza A Virus Hemagglutinin after Recent Natural Infection", Journal of Virology, 1995, vol. 69, p. 7497-7506.
European Patent Office, "Communication Pursuant to Article 94(3) EPC" regarding EP Appl. No. 04 810 256.0, Dated Nov. 30, 2009, 3—pages. T. O. Cameron et al., Examination of the Highly Diverse CD4+ T-Cell Repertoire Directed Against an Influenza Peptide: A Step Towards TCR Proteomics, Immunogenetics (2002) vol. 54, 611-620.
C.M. Gelder et al., Human CD4+ T-Cell Recognition of Influenza A Virus Hemagglutinin After Subunit Vaccination, Journal of Virology (1996) vol. 70 (7), 4787-4790.
C. Gelder et al., Six Unrelated HLA-DR-Matched Adults Recognize Identical CD4+ T Cell Epitopes from Influenza A Haemagglutinin That are not Simply Peptides With High HLA-DR Binding Affinities, International Immunology (1998) vol. 10 (2), 211-222.

(Continued)

*Primary Examiner* — Zachariah Lucas
*Assistant Examiner* — Nicole Kinsey White
(74) *Attorney, Agent, or Firm* — Olson & Cepuritis, Ltd.

(57) ABSTRACT

The present invention provides compositions useful for treating or preventing influenza infections. The composition comprises an isolated polypeptide including a sequence of at least 8 contiguous amino acid residues of the fusion initiation region (FIR) of an influenza hemagglutinin 2 protein or a peptide analog of the sequence. The FIR is a segment of the full length hemagglutinin 2 protein which is bounded by an amino-terminal region within the amino-terminal alpha-helix thereof and a carboxy terminus within the carboxy-terminal alpha-helix thereof, with a cysteine loop therebetween. The amino-terminal region of the FIR comprises a portion of the final 10 to 20 amino acid residues of the amino-terminal alpha-helix of the hemagglutinin 2 protein, and includes 3 or 4 hydrophobic amino acid residues, a positively-charged amino acid residue, a negatively-charged amino acid residue, and an aromatic amino acid residue. The carboxy terminus of the FIR is the carboxy terminus of the first peptide sequence of the hemagglutinin 2 protein beyond the amino terminal helix, which exhibits a positive Wimley-White interfacial hydrophobicity.

20 Claims, 23 Drawing Sheets

OTHER PUBLICATIONS

C. Gelder et al., Associations Between Human Leukocyte Antigens and Nonresponsiveness to Influenza Vaccine, Journal of Infectious Diseases (2002) vol. 185, 114-117.

C.A. Janeway, Jr. et al., Synthetic Peptides of Protective Antigens Can Elicit Protective Immunity, Immuno Biology 5, The Immune System in Health and Disease (2001), 586-587.

D. N. Levy et al., Synthetic Peptide-Based Vaccines and Antiviral Agents Including HIV/AIDS as a Model System, Biologically Active Peptides: Design, Synthesis, and Utilization (1993) vol. 1, 219-266.

B. Lina et al., A TritonX-100-Split Virion Influenza Vaccine is Safe and Fulfills the Committee for Proprietary Medicinal Products (CPMP) Recommendations for the European Community for Immunogenicity, in Children, Adults and the Elderly, Biologicals (2000) vol. 28, 95-103.

X. Lu et al., A Mouse Model for the Evaluation of Pathogenesis and Immunity to Influenza A (H5N1) Viruses Isolated from Humans, Journal of Virology (1999) vol. 73 (7), 5903-5911.

D. C. Powers et al., Humoral and Cellular Immune Responses Following Vaccination with Purified Recombinant Hemagglutinin from Influenza A (H3N2) Virus, The Journal of Infectious Diseases (1997) vol. 175, 342-351.

P. Steigerwald-Mullen et al., Type 2 Cytokines Predominate in the Human CD4+T-Lymphocyte Response to Epstein-Barr Virus Nuclear Antigen 1, Journal of Virology (2000) vol. 74 (15), 6748-6759.

O. M. Williams et al., Analysis of CD4+ T-Cell Responses to Human Papillomavirus (HPV) Type 11 L1 in Healthy Adults Reveals a High Degree of Responsiveness and Cross-Reactivity with Other HPV Types, Journal of Virology (2002) vol. 76 (15), 7418-7429.

* cited by examiner

FIG. 2, Panel A

FIG. 2, Panel B

FIG. 2, Panel C

FIG. 2, Panel D

Influenza B Hemagglutinin 2

```
GFFGAIAGFL    EGGWEGMIAG    WHGYTSHGAH
GVAVAADLKS    TQEAINKITK    NLNSLSELEV
KNLQRLSGAM    DELHNEILEL    DEKVDDLRAD
TISSQIELAV    LLSNEGIINS    EDEHLLALER
KLKKMLGPSA    VDIGNGCFET    KHKCNQTCLD
RIAAGTFNAG    EFSLPTFDSL    NITAASLNDD
GLDNHTILLY    YSTAASSLAV    TLMIAIFIVY
MVSRDNVSCS    ICL
```

CYTOPLASM
RNP ENTRY

CYTOPLASM
H+
H+
H+
VESICLE

Influenza virus

CYTOPLASM
sialolipid or sialoprotein receptor
HA1
HA2

Influenza virus

FIG. 14

INFLUENZA INHIBITING COMPOSITIONS AND METHODS

CROSS REFERENCE TO RELATED APPLICATIONS

This application is a continuation of International Application Serial No. PCT/US2008/007918, filed on Jun. 25, 2008, which claims the benefit of U.S. Provisional Application Ser. No. 60/937,120, filed Jun. 25, 2007, each of which is incorporated herein by reference in its entirety.

FIELD OF INVENTION

The present invention relates to compositions comprising peptides effective for preventing or inhibiting viral infection of a cell by an influenza virus, and to methods of treating or preventing influenza infections therewith.

BACKGROUND OF THE INVENTION

All viruses must bind to and invade their target cells to replicate. For enveloped viruses, including RNA viruses having Class I membrane fusion proteins, the process involves (a) the binding of the virion to the target cell, (b) fusion of the envelope of the virus with the plasma membrane or an internal cellular membrane, (c) destabilization of the viral envelope and cellular membrane at the fused area to create a fusion pore, (d) transfer of the viral RNA through the pore, and (e) modification of cellular function by the viral RNA.

Steps (b) and (c) above, which involve the fusion of the viral membrane and the cell envelope, are mediated by the interaction of a viral transmembrane glycoprotein (fusion protein) with surface proteins and membranes of the target cell. These interactions cause conformal changes in the fusion protein that result in the insertion of a viral fusion peptide into the target cell membrane. This insertion is followed by further conformational changes within the fusion protein that bring the viral envelope and cell membranes into close proximity and results in the fusion of the two membrane bilayers.

A virus is unable to spread and propagate within its host if this fusion process is disrupted. Intentional disruption of this fusion process can be achieved by directing peptides and peptide mimics homologous to fusion protein sequences, antibodies that recognize the fusion protein, and other factors that act against the fusion protein.

Hemagglutinin 2 (HA2) an envelope protein of the influenza virus, an orthomyxovirus, is the prototypic RNA virus Class I fusion protein. HA2 contains an amino terminal hydrophobic domain, referred to as the fusion peptide, that is exposed during cleavage of the hemagglutinin precursor protein. Retroviral transmembrane proteins contain several structural features in common with the known structure of HA2 in addition to the fusion peptide, including an extended amino-terminal helix (N-helix, usually a "heptad repeat" or "leucine zipper"), a carboxy-terminal helix (C-helix), and an aromatic motif proximal to the transmembrane domain. The presence of at least four out of these five domains define a viral envelope protein as a Class I fusion protein.

FIG. 1 shows the five previously-described domains of the fusion proteins of the six families of Class I viruses. The fusion proteins originate in a hydrophobic fusion peptide, terminate in an anchor peptide, and incorporate an extended amino terminal alpha-helix (N-helix, usually a "heptade repeat" or "leucine zipper"), a carboxy-terminal alpha-helix (C-helix), and sometimes an aromatic motif proximal to the virion envelope. Also shown for each of the viral families is a sixth domain, referred to herein as the fusion initiation region (FIR), which was discovered by the present inventors and disclosed in U.S. Ser. No. 10/578,013.

About 10 to 20 percent of the population of the United States suffers from seasonal influenza each year. While most individuals recover from influenza in one to two weeks, the very young, the elderly, and persons with chronic medical conditions can develop post-flu pneumonia and other lethal complications. The causative agent of influenza is the influenza virus, an orthomyxovirus which readily develops new strains through a process of reassortment and mutation of the segmented viral genome.

Highly virulent strains of type A influenza virus can produce epidemics and pandemics. In recent years, there has been an emergence of a highly pathogenic strain of avian influenza A virus subtype H5N1 capable of inflicting a high mortality rate. Because of the threat posed by the influenza virus both to public health and as a potential agent of bioterrorism, developing therapeutics to control seasonal influenza and the increasing threat of pandemic influenza is a high priority.

SUMMARY OF THE INVENTION

The present invention provides peptides, peptide analogs, peptide derivatives and pharmaceutical compositions useful for treating or preventing influenza infections and/or preventing the person-to-person transmission of an influenza infection. A peptide of the invention comprises an influenza virus-cell fusion inhibiting portion of the fusion initiation region (FIR) of a wild-type influenza hemagglutinin 2 protein or a variant thereof. The variant differs from the wild-type protein by selected substitutions in the amino acid residue sequence of the wild-type hemagglutinin 2 protein sequence.

In a first embodiment, an isolated peptide of the invention consists of 8 to 40 consecutive amino acid residues of a portion of a selected wild-type influenza hemagglutinin 2 protein or a variant thereof. The portion of the hemagglutinin 2 protein comprises the fusion initiation region (FIR) of the protein and up to five amino acid residues on the amino-terminal and carboxy-terminal sides of the FIR. The portion also includes at least the sequence YNAELL (SEQ ID NO: 1) or a variant thereof that differs from SEQ ID NO: 1 by one or more amino acid substitutions selected from the group consisting of Y1S, Y1T, Y1W, Y1A, N2Q, A3L, A3I, A3V, E4D, E4K, E4R, E4H, L5I, L5V, L5A, L6I, L6V, and L6A.

In this first embodiment, the variant differs from the selected wild-type sequence by one or more amino acid substitutions in the amino acid sequence of the portion of the selected wild-type protein referred to above. The substitutions can be selected from corresponding amino acid residues of other wild-type influenza hemagglutinin 2 proteins or conservative substitutions of the wild-type residues, and preferably are selected so as to maintain a Wimley-White interfacial hydropathy profile for the variant having local maxima and local minima in the profile within about 5 amino acid residues of the local maxima and local minima of the Wimley-White interfacial hydropathy profile of the corresponding region of at least one wild-type hemagglutinin 2 amino acid sequence. Preferably the variant of the selected wild-type sequence shares at least 50 percent sequence identity with the wild-type sequence.

In a second embodiment, a peptide of the invention comprises an 8 to 40 amino acid residue portion of the FIR of a wild-type influenza A or influenza B hemagglutinin 2 protein from a region of the protein in the range of residues 72 to 113, or a variant thereof that differs from residues 72 to 113 of the wild-type sequence by one or more amino acid residue substitutions in the wild-type sequence. The substitutions in the variant are selected from corresponding amino acid residues of other wild-type hemagglutinin 2 proteins or conservative substitutions thereof, and preferably are selected to preserve the overall form of the Wimley-White hydropathy profile of the peptides i.e., to maintain a Wimley-White hydropathy profile for the variant having local maxima and local minima within about 5 amino acid residues of the local maxima and local minima of the Wimley-White hydropathy profile of the corresponding wild-type hemagglutinin 2 amino acid sequence. Preferably, the variants in this embodiment differ from the wild-type sequence by a conservative substitution.

In a third embodiment, a peptide of the invention consists of 8 to 40 consecutive amino acid residues of the amino acid sequence of SEQ ID NO: 2 (EVEGRIQDLEKYVEDT-KIDLWSYNAELLVALENQHTIDLTDS) or a variant thereof. SEQ ID NO: 2 encompasses amino acid residues 72 to 113 of the hemagglutinin 2 protein of the wild-type influenza A subtype H3 (SEQ ID NO: 19). The 8 to 40 amino acid peptide comprises at least amino acid residues 23 to 28 of SEQ ID NO: 2 or of the variant. In this embodiment, the variant differs from SEQ ID NO: 2 by one or more amino acid substitutions selected from the group consisting of E1D, E1N, E1Q, V2G, V2S, V2T, V2I, V2L, V2A, V2M, V2C, E3D, E3N, E3Q, G4T, G4S, G4K, G4R, G4H, G4Q, G4N, R5K, R5H, R5Q, R5N, I6L, I6V, I6A, I6M, I6C, Q7N, Q7E, Q7D, Q7G, Q7S, Q7T, D8E, D8N, D8Q, D8M, D8C, L9I, L9V, L9A, L9M, L9C, E10D, E10N, E10Q, E10I, E10L, E10V, E10A, E10M, E10C, K11R, K11H, K11D, K11E, K11N, K11Q, Y12W, Y12K, Y12R, Y12H, V13I, V13L, V13A, V13G, V13T, V13S, V13M, V13C, E14D, E14K, E14R, E14H, D15E, D15R, D15N, D15Q, T16G, T16S, T16A, T16Q, T16N, K17F, K17R, K17M, K17C, K17I, K17V, K17L, K17A, I18L, I18V, I18A, I18T, I18S, I18G, I18Q, I18N, D19E, D19N, D19Q, L20I, L20V, L20A, L20C, L20M, W21Y, W21A, S22T, S22G, S22A, S22M, S22C, Y23W, Y23S, Y23T, Y23A, N24Q, N24D, N24E, A25I, A25V, A25L, A25M, E26D, E26K, E26R, E26H, L27A, L27I, L27V, L27M, L28I, L28V, L28A, L28M, V29I, V29L, V29A, V29M, A30I, A30L, A30V, A30M, A30C, L31I, L31V, L31A, L31M, L31C, E32D, E32N, E32Q, N33Q, N33Q, Q34E, N33E, Q34E, Q34D, Q34G, Q34S, Q34T, H35K, H35R, H35N, H35Q, T36G, I37L, I37V, I37A, I37M, I37C, D38E, D38N, D38Q, L39F, L39I, L39V, L39M, L39C, L39A, L39E, L39D, L39N, L39Q, T40H, T40R, T40K, T40S, T40G, T40A, T40M, D41E, D41N, D41Q, S42G, S42T, S42I, S42L, S42V, S42A, S42M, and S42C.

In certain preferred embodiments, the peptide of the invention is a peptide consisting of at least 8 consecutive amino acid residues of any of the sequences SEQ ID NO: 3-13, which represent portions of the FIR of a wild-type influenza A hemagglutinin 2 (HA2) or influenza B hemagglutinin (HB) protein. In other preferred embodiments, the peptide consists of at least 8 amino acid consecutive residues of a variant of any one of SEQ ID NO: 3-13. In this alternative embodiment, the variant differs from the selected sequence by one or more amino acid substitutions, preferably conservative substitutions, analogous to those described in the third embodiment discussed above.

When administered to the nasal cavities of ferrets, a peptide of the invention, referred to herein as flu inhibitor-3 (F3) effectively blocked development of influenza in the animals and transmission of influenza from animal to animal. The amino acid sequence of F3 is identical to residues 84-99 of the HA2 of most influenza A H3 subtype viruses, including A/H3N2 strains currently circulating in humans. F3 also is active against a recombinant H5N1 influenza virus and against two strains of influenza B (B/Shanghai/361/2002 and B/Shanghai/10/2003), in vitro, in immunoplaque assays with $IC_{50}$ in the low mM range (<5 nM). Given the diversity of these different influenza A and B strains, F3 is likely to be effective against most influenza viruses.

In other aspects, the present invention provides analogs of a peptide of the invention (e.g., cyclic peptides, or peptides containing a non-natural amino acid), derivatives of a peptide or an analog of the invention in which the peptide or analog includes a non-HA2-derived group bound to a residue of the peptide (e.g., a lipid or a non-influenza HA2 peptide sequence), and an isolated antibody that is specific for (i.e., is capable of specifically and selectively binding to) a peptide, analog, or derivative of the invention.

Another aspect of the invention is the use of a peptide, analog, derivative or antibody of the invention in a therapeutic method for treating or preventing an influenza infection. This use can include the use of the peptide, analog, derivative or antibody of the invention to prepare a medicament for treating influenza. The peptides, analogs, derivatives, and antibodies of the invention can be included in a pharmaceutical composition in combination with a pharmaceutically acceptable carrier.

BRIEF DESCRIPTION OF THE DRAWINGS

FIG. 2 shows a sequence alignment of HA2 variants H1 (SEQ ID NO: 17), H2 (SEQ ID NO: 18), H3 (SEQ ID NO: 19), H4 (SEQ ID NO: 20), H5 (SEQ ID NO: 21), H6 (SEQ ID NO: 22), H7 (SEQ ID NO: 23), H9 (SEQ ID NO: 24), H10 (SEQ ID NO: 25), H13 (SEQ ID NO: 26), H14 (SEQ ID NO: 27), H15 (SEQ ID NO: 28), and H16 (SEQ ID NO: 29).

FIG. 3 shows the amino acid residue sequence of influenza B hemagglutinin 2, B/Yamagata/16/1988 (SEQ ID NO: 30).

FIG. 4 shows a comparison of residues 72-113 of influenza A and influenza B hemagglutinin 2 proteins, specifically residues 72-113 of influenza A subtypes H1 (SEQ ID NO: 17), H2 (SEQ ID NO: 18), H3 (SEQ ID NO: 19), H4 (SEQ ID NO: 20), H5 (SEQ ID NO: 21), H6 (SEQ ID NO: 22), H7 (SEQ ID NO: 23), H9 (SEQ ID NO: 24), H10 (SEQ ID NO: 25), H13 (SEQ ID NO: 26), H14 (SEQ ID NO: 27), H15 (SEQ ID NO: 28), H16 (SEQ ID NO: 29), and of influenza B/Yamagata/16/1988 hemagglutinin 2 (SEQ ID NO: 30).

Figure 14:
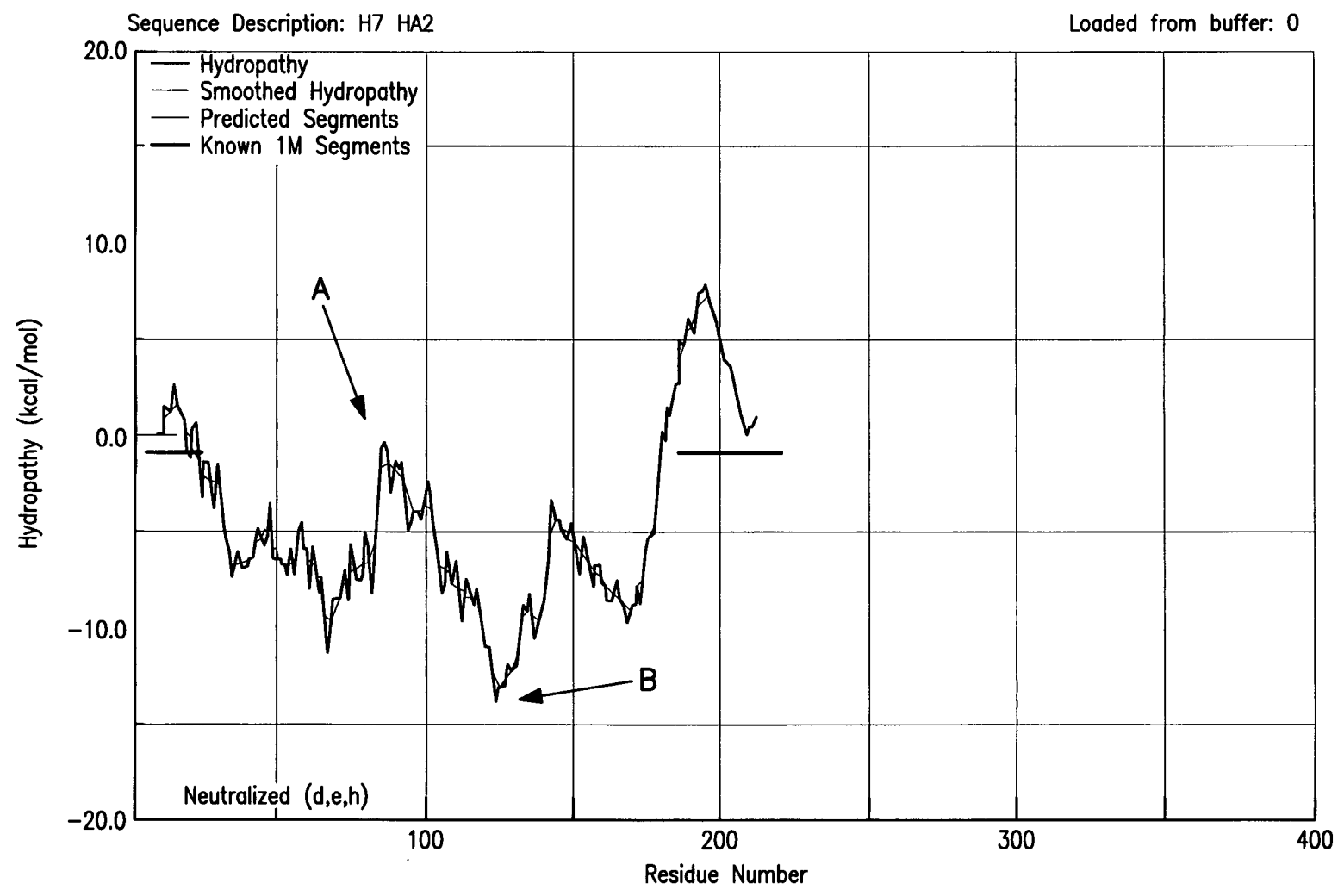

FIG. 14 shows a Wimley-White interfacial hydropathy plot for Influenza A H7 hemagglutinin 2.

DETAILED DESCRIPTION OF THE PREFERRED EMBODIMENTS

Figure 1:
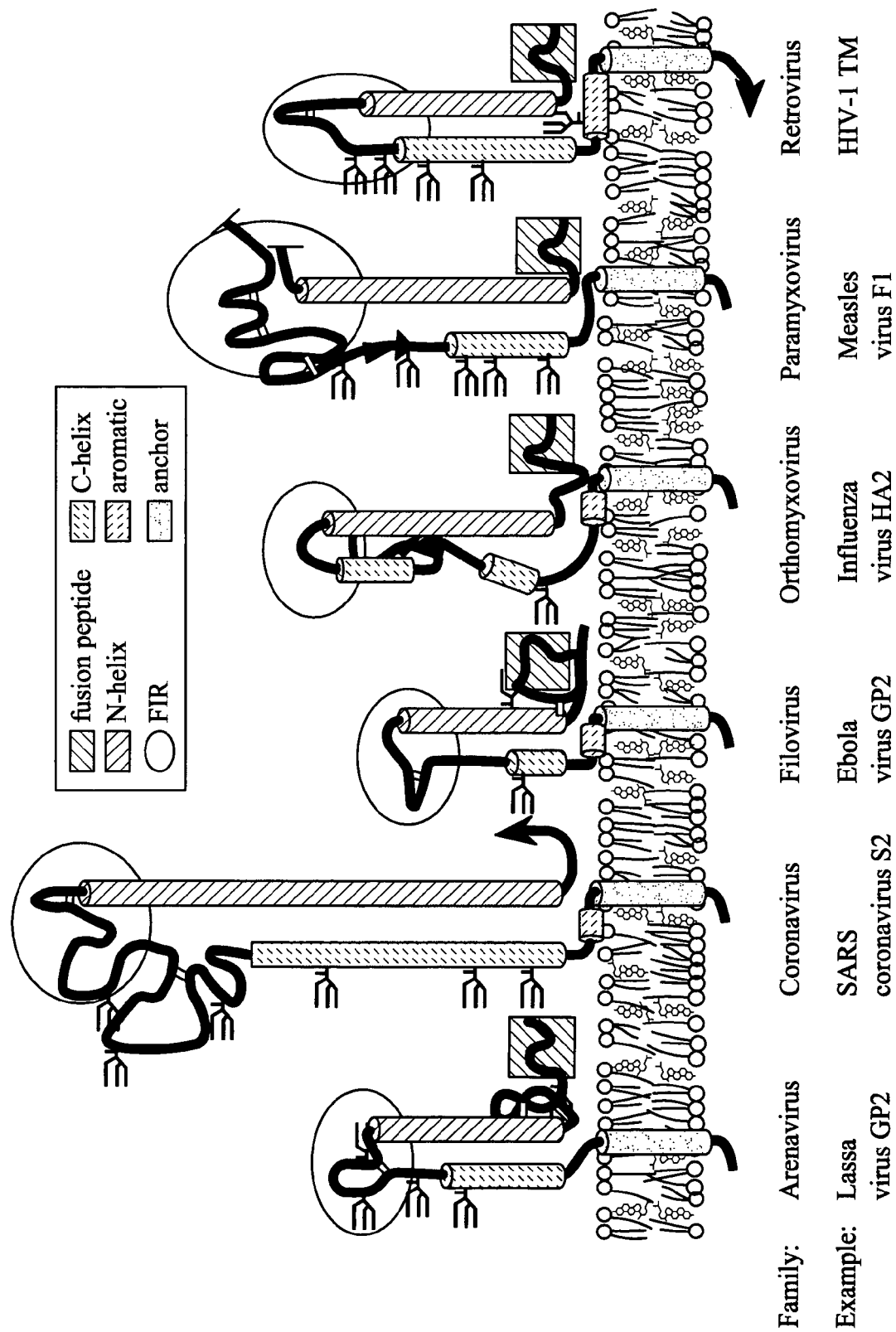
FIG. 1 shows the five previously identified domains of the fusion proteins from the six families of Type I viruses, as well as the sixth domain known as the fusion initiation region (FIR).
Figure 5C:
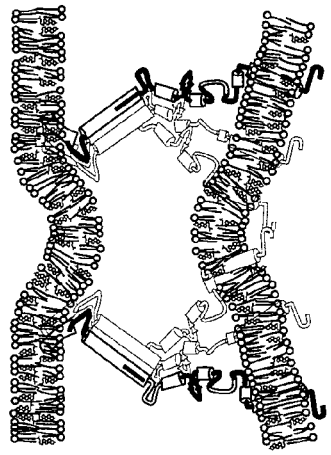
FIG. 5 shows a potential mechanism for virus-cell fusion.
Figure 5E:
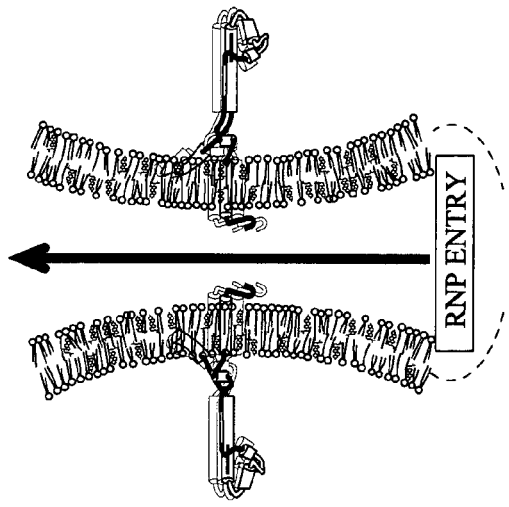
Figure 5B:
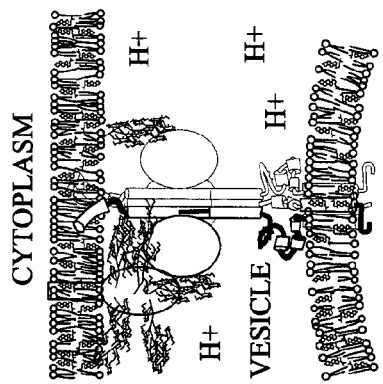
Figure 5D:
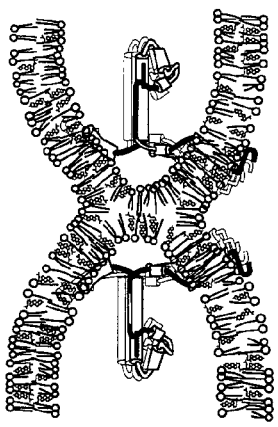
Figure 5A:
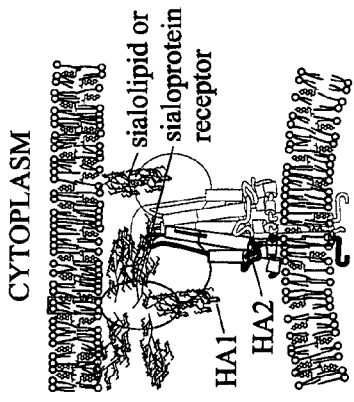
Figure 5C:
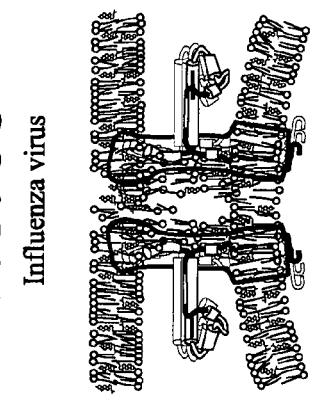

The present invention provides peptides, peptide analogs, peptide derivatives, antibodies, and pharmaceutical compositions useful for treating or preventing influenza infections or preventing the person-to-person transmission of an influenza infection. The present invention utilizes peptides having amino acid sequence similarities to portions of the fusion initiation region (FIR) of wild-type influenza hemagglutinin 2 proteins. The peptides of the invention can inhibit influenza virus-cell fusion, and thereby treat and/or prevent influenza infections. The peptides of the invention can comprise selected portions of wild-type influenza virus hemagglutinin 2 proteins in the region of the FIR, or variants of the selected portions. The variants differ from the wild-type protein by selected substitutions in the amino acid residue sequence of the wild-type hemagglutinin 2 protein sequence. While not wishing to be bound by theory, it is believed that the peptide of the invention prevents and treats influenza infections by interfering with the normal interaction of the FIR domain of a viral fusion peptide with a target cell surface, e.g. by interfering with protein aggregation or conformal changes required for activation or fusion.

In a first embodiment, an isolated peptide of the invention consists of 8 to 40 consecutive amino acid residues, preferably 9 to 16 consecutive amino acid residues, of a portion of a selected wild-type influenza hemagglutinin 2 protein comprising the fusion initiation region (FIR) of the protein and up to five amino acid residues on the amino-terminal and carboxy-terminal sides of the FIR, or a variant thereof. The 8 to 40 amino acid peptide includes at least the sequence YNAELL (SEQ ID NO: 1) or a variant thereof that differs from SEQ ID NO: 1 by one or more amino acid substitutions selected from the group consisting of Y1S, Y1T, Y1W, Y1A, N2Q, A3L, A3I, A3V, E4D, E4K, E4R, E4H, L5I, L5V, L5A, L6I, L6V, and L6A. SEQ ID NO: 1 represents one of the most highly conserved portions of the FIR all of the characterized influenza A hemagglutinin 2 proteins (i.e., residues 94 to 99 of the influenza A hemagglutinin 2 sequences). The amino acid sequence of the FIR includes that portion of the selected wild-type hemagglutinin 2 protein beginning at about residue 77 in the N-helix of the protein, and ending at a residue in the range of residue 110 to residue 119 of the selected wild-type hemagglutinin 2 protein. The carboxy-terminal end of the influenza FIR, as described herein, is the residue immediately preceding the first residue beyond residue 104 (the carboxy-terminus of the N-helix) that begins a region of increasing Wimley-White interfacial hydrophobicity. Put another way, the FIR is characterized by a sequence of amino acid residues that exhibit a peak in the Wimley-White interfacial hydropathy profile of the wild-type hemagglutinin 2 protein, beginning in the N-helix (at residue 77) and ending within about 15 residues after the carboxy-terminus of the N-helix. The carboxy terminus of the peak region (i.e., the FIR) is characterized by a local minimum in the hydropathy profile. The residue immediately following the local minimum at the carboxy-terminus of the FIR begins another peak in the hydropathy profile (i.e., a region of increasing interfacial hydrophobicity).

Figure 2:
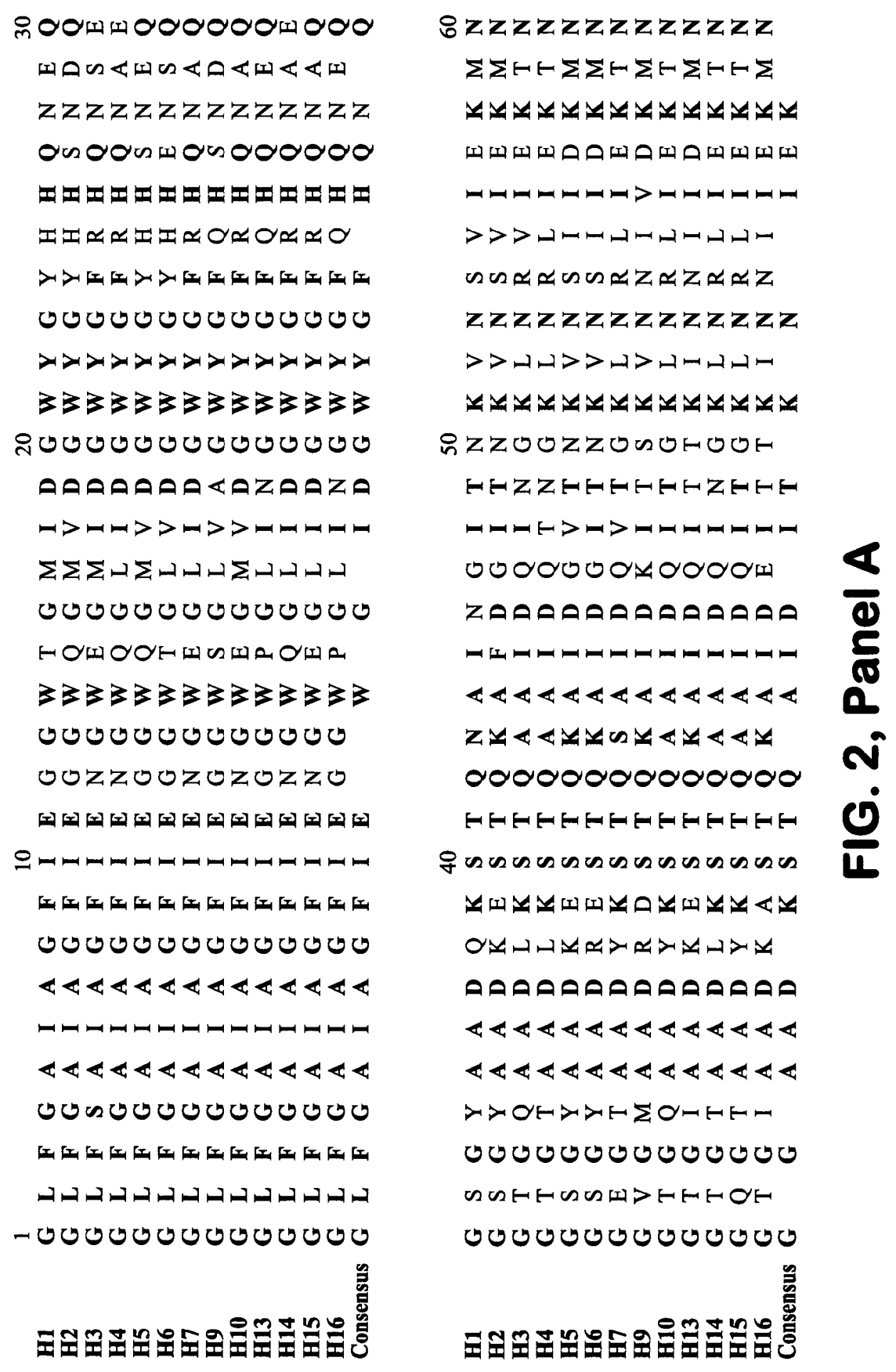
Figure 2:
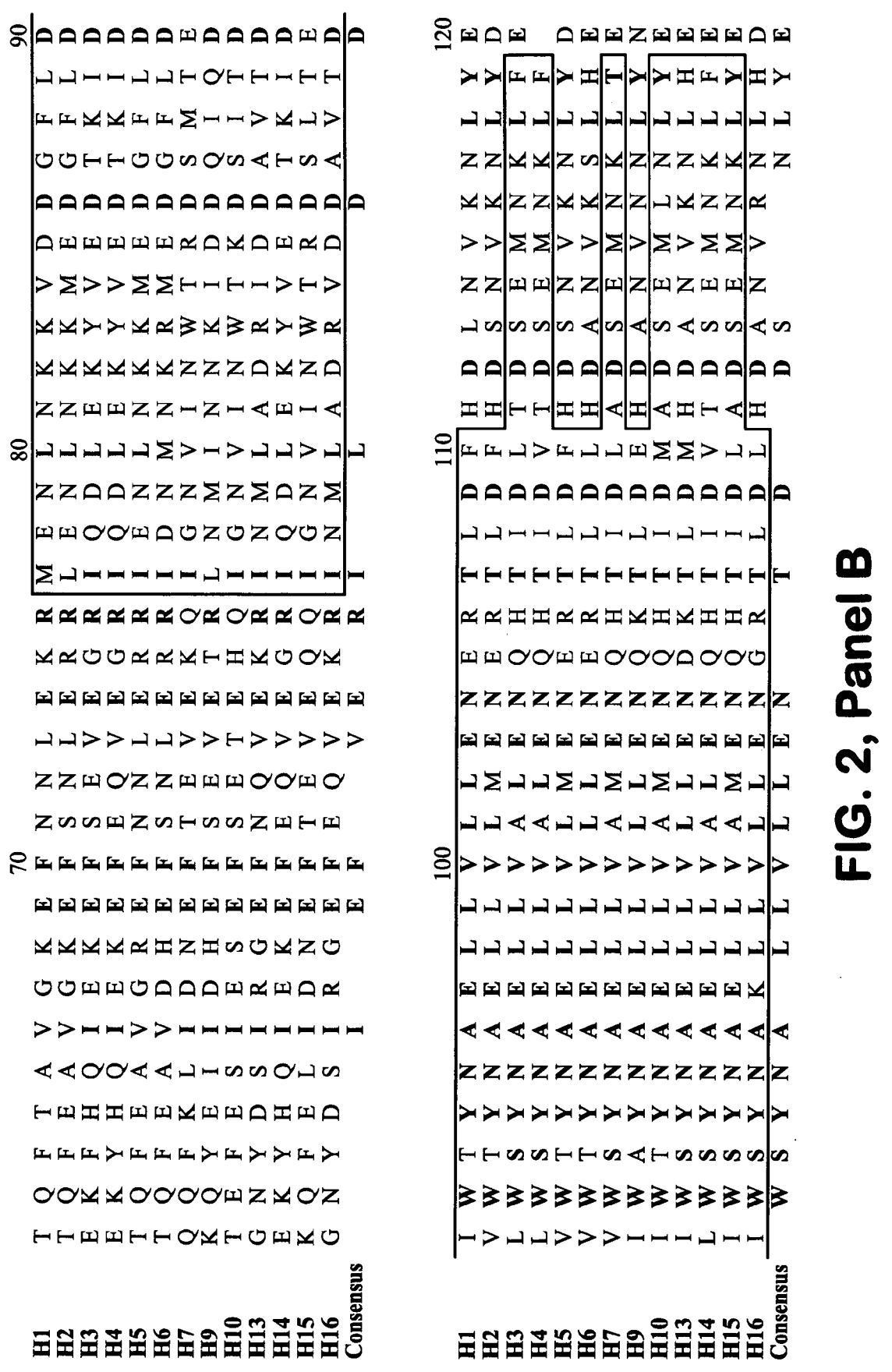
Figure 2:
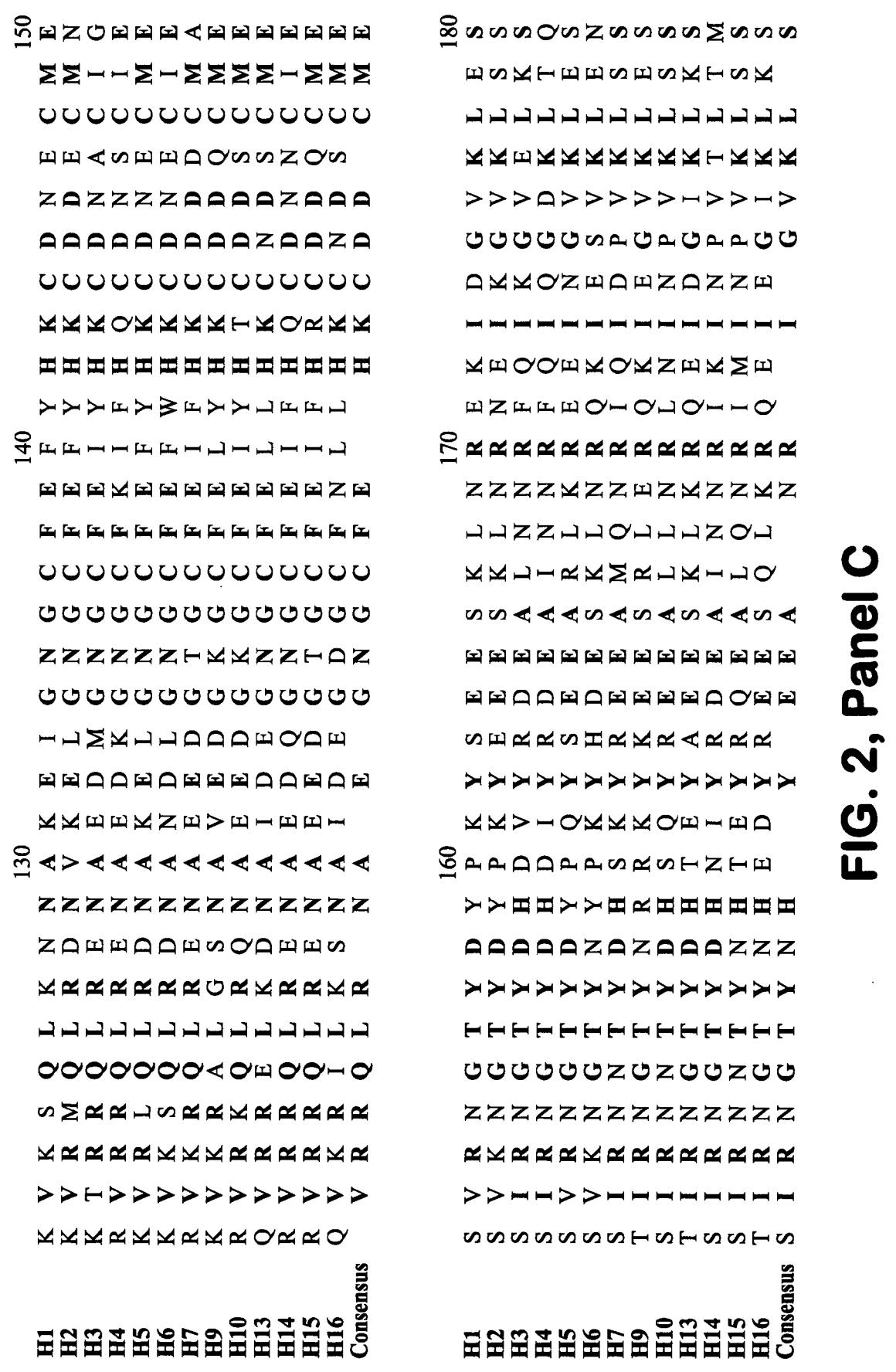

In this first embodiment, the variant differs from the selected wild-type sequence by one or more amino acid substitutions in the amino acid sequence of the portion of the selected wild-type protein referred to above. The substitutions are selected from corresponding amino acid residues of other wild-type influenza hemagglutinin 2 proteins or conservative substitutions of the corresponding residues, and preferably are selected so as to maintain a Wimley-White interfacial hydropathy profile for the variant having local maxima and local minima in the profile within about 5 amino acid residues of the local maxima and local minima of the Wimley-White interfacial hydropathy profile of the corresponding region of at least one wild-type hemagglutinin 2 FIR amino acid sequence. For example, the wild-type hemagglutinin 2 can be from a subtype selected from the group consisting of the H1, H2, H3, H4, H5, H6, H7, H9, H10, H11, H12, H13, H15, and H16 variants of influenza A hemagglutinin 2 (SEQ ID NO: 17-29), or can be from an influenza B hemagglutinin 2 protein (SEQ ID NO: 30). The amino acid sequences of influenza A hemagglutinin 2 subtypes H1, H2, H3, H4, H5, H6, H7, H9, H10, H11, H12, H13, H15, and H16 are shown in FIG. 2, with the FIR regions enclosed in a black outline. The amino acid sequence of influenza B hemagglutinin 2 (SEQ ID NO: 30) is shown in FIG. 3. Preferably, the variant of the selected wild-type sequence shares at least 50 percent sequence identity (e.g., at least 60%, at least 70% or at least 80% sequence identity) with the wild-type sequence.

In a second embodiment, a peptide of the invention comprises 8 to 40, preferably 9 to 16, consecutive amino acid residues of residues 72 to 113 of the FIR of a wild-type influenza A or influenza B hemagglutinin 2 protein, or a variant thereof that differs from residues 72 to 113 of the wild-type sequence by one or more amino acid residue substitutions. The substitutions in the variant are selected from corresponding amino acid residues of other wild-type hemagglutinin 2 proteins or conservative substitutions thereof, and preferably are selected to preserve the overall form of the Wimley-White hydropathy profile of the wild-type peptide, i.e., to maintain a Wimley-White hydropathy profile for the variant having local maxima and local minima within about 5 amino acid residues of the local maxima and local minima of the Wimley-White hydropathy profile of the corresponding wild-type hemagglutinin 2 amino acid sequence. For example, preferably, the variants in this embodiment contain conservative substitutions of certain wild-type amino acid residues.

As used herein, the term "conservative substitutions" and grammatical variations thereof, refers to the presence of an amino acid residue in the sequence of the peptide that is different from, but is in the same class of amino acid as the wild-type residue (i.e., a nonpolar residue replacing a nonpolar residue, an aromatic residue replacing an aromatic residue, a polar-uncharged residue replacing a polar uncharged residue, a charged residue replacing a charged residue). In addition, conservative substitutions can encompass a residue having an interfacial hydropathy value of the same sign and generally of similar magnitude as the wild-type residue that it replaces.

As used herein, the term "nonpolar residue" refers to glycine, alanine, valine, leucine, isoleucine, and proline; the term "aromatic residue" refers to phenylalanine, tyrosine, and tryptophan; the term "polar uncharged residue" refers to serine, threonine, cysteine, methionine, asparagine and glutamine; the term "charged residue" refers to the negatively charged amino acids aspartic acid and glutamic acid, as well as the positively charged amino acids lysine, arginine, and histidine.

Figure 4:
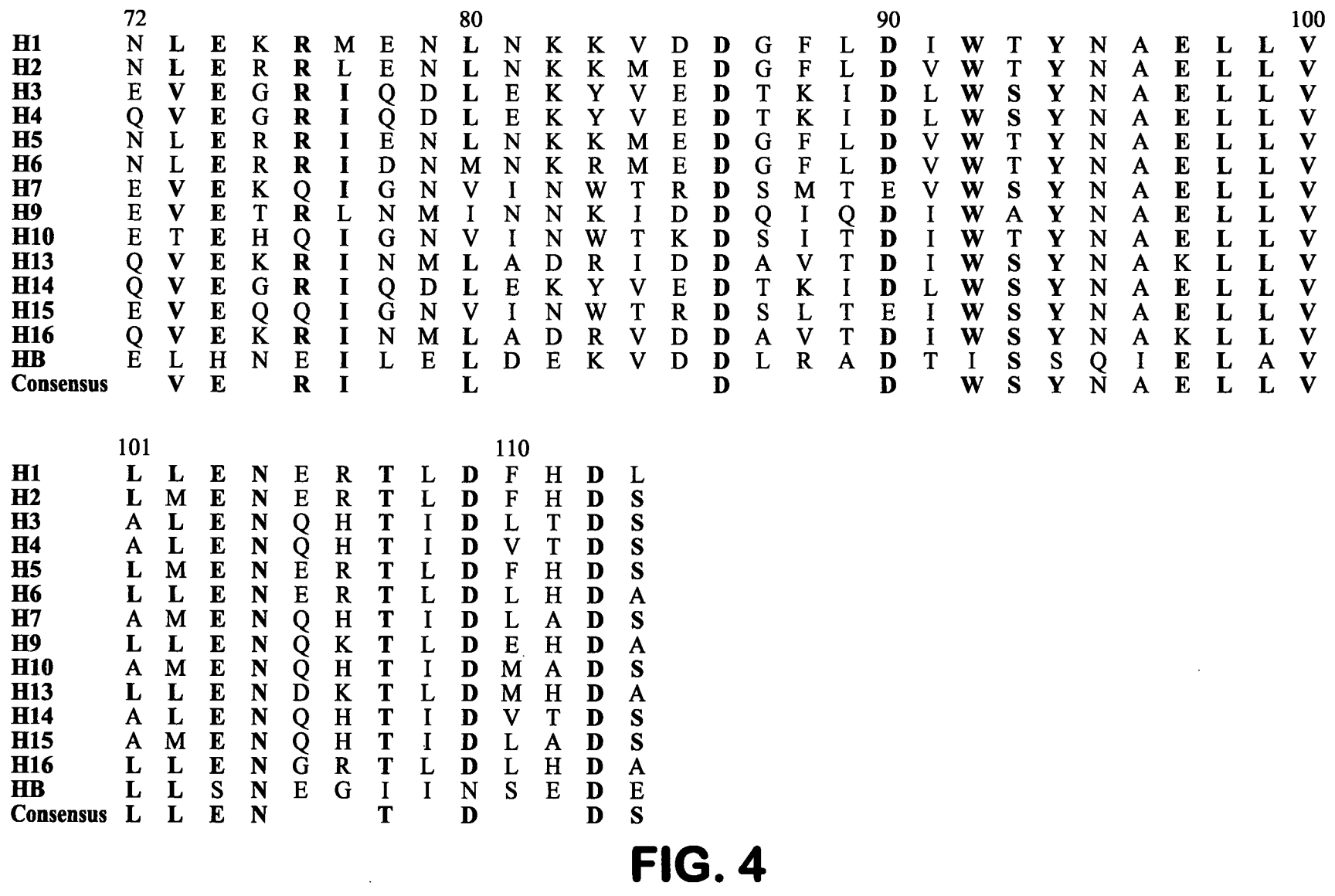

FIG. 4 compares residues 72-113 of each of the influenza A hemagglutinin 2 subtypes shown in FIG. 2, along with the corresponding region of the influenza B hemagglutinin 2 (i.e., residues 72-113 of SEQ ID NO: 30). As is evident in FIG. 4, there are significant sequence similarities between the different hemagglutinin subtypes. The region of residues 72-113 of each of the influenza A hemagglutinin 2 subtypes shares 50 percent or greater sequence identity to the corresponding region of the H3 subtype (i.e., SEQ ID NO: 2). The percentage sequence identities between SEQ ID NO: 2 and residues 72-113 of the various other subtypes are as follows: H4 and H14 share about 95.2% sequence identity with SEQ ID NO: 2; H7 and H15 share about 59.5% sequence identity with SEQ ID NO: 2; H10 and H16 share about 54.7% sequence identity with SEQ ID NO: 2; H5 and H6 share about 52% sequence identity with SEQ ID NO: 2; and H1, H2, H9 and H13 share 50% sequence identity with SEQ ID NO: 2. Residues 72-113 of the influenza B hemagglutinin 2 shares about 30.9% sequence identity with SEQ ID NO: 2; however, the differences between SEQ ID NO: 2 and residues 72-113 of the influenza B protein are predominately conservative substitutions.

As is evident from FIG. 2, FIG. 3, and FIG. 4, the known wild-type hemagglutinin 2 proteins collectively have amino acid residues at positions in the range of residues 72-113 that belong to more than one class of amino acid. Accordingly, in such a case, the variants of the peptides of the invention may also include amino acid substitutions from more than one class of amino acid at such positions. Preferably, the variant of the selected wild-type sequence shares at least 50 percent sequence identity (e.g., at least 60%, at least 70% or at least 80% sequence identity) with the wild-type sequence.

In a third embodiment, a peptide of the invention consists of 8 to 40 consecutive amino acid residues, preferably 9 to 16 consecutive amino acid residues, of the amino acid sequence of SEQ ID NO: 2 (EVEGRIQDLEKYVEDTKIDLWSYN AELLVALENQHTIDLTDS) or a variant thereof. SEQ ID NO: 2 is a portion of the wild-type influenza A subtype H3 hemagglutinin 2 protein encompassing amino acid residues 72 to 113 thereof. In this embodiment, the peptide comprises at least amino acid residues 23 to 28 of SEQ ID NO: 2 or of the variant thereof, and the variant differs from SEQ ID NO: 2 by one or more amino acid substitutions. The one or more amino acid residue substitutions in the variant sequence are selected from the group of substitutions shown in Table 1. Preferably, the variant shares at least 50 percent sequence identity (e.g., at least 60%, at least 70% or at least 80% sequence identity) with SEQ ID NO: 2. In Table 1, the first column of substitutions are preferred, the second column of substitutions are more preferred and are more conservative than those in the first column, while the third column of substitutions are alternatives that can be included in the peptides of the invention.

TABLE 1

Substitutions in SEQ ID NO: 2.

| Position | Preferred Substitutions | More Preferred Substitutions | Alternative Preferred Substitutions |
|---|---|---|---|
| 1 | E1D, E1N, E1Q | E1D, E1N, E1Q | |
| 2 | V2G, V2S, V2T, V2I, V2L, V2A, V2M, V2C | V2S, V2T, V2I, V2L, V2A, V2M | |
| 3 | E3D, E3Q, E3N | E3D | |
| 4 | G4T, G4S, G4K, G4R, G4H, G4Q, G4N | G4T, G4S, G4K, G4R, G4H, G4Q, G4N | |
| 5 | R5K, R5H, R5Q, R5N | R5K, R5Q, R5N | |
| 6 | I6L, I6V, I6A, I6M, I6C | I6L, I6V, I6A, I6M | |
| 7 | Q7N, Q7E, Q7D, Q7G, Q7S, Q7T | Q7N, Q7E, Q7D, Q7G | |
| 8 | D8E, D8N, D8Q, D8M, D8C | D8E, D8N, D8Q, D8M | |
| 9 | L9I, L9V, L9A, L9M, L9C | L9I, L9V, L9A, L9M | |
| 10 | E10D, E10N, E10Q, E10I, E10L, E10V, E10A, E10M, E10C | E10D, E10N, E10Q, E10I, E10L, E10V, E10A | |
| 11 | K11R, K11H, K11D, K11E, K11N, K11Q | K11R, K11D, K11E, K11N, K11Q | |
| 12 | Y12W, Y12K, Y12R, Y12H | Y12W, Y12K, Y12R | |
| 13 | V13I, V13L, V13A, V13G, V13T, V13S, V13M, V13C | V13I, V13L, V13A, V13G, V13T, V13S, V13M | |
| 14 | E14D, E14K, E14R, E14H | E14D, E14K, E14R | E14D, E14R |
| 15 | D15E, D15R, D15N, D15Q | D15E | D15E, D15R |
| 16 | T16G, T16S, T16A, T16Q, T16N | T16G, T16S, T16Q, T16N, | I16A |
| 17 | K17F, K17R, K17M, K17C, K17I, K17V, K17L, K17A | K17F, K17M, K17I, K17V, K17L, K17A, | K17R |
| 18 | I18L, I18V, I18A, I18T, I18S, I18G, I18Q, I18N | I18L, I18V, I18A, I18T, I18S, I18Q, I18N | I18A |
| 19 | D19E, D19N, D19Q | D19E | D19E |
| 20 | L20I, L20V, L20A, L20M, L20C | L20I, L20V, L20A | L20A |
| 21 | W21Y, W21A | W21Y | W21Y, W21A |
| 22 | S22T, S22G, S22A, S22M, S22C | S22T, S22G, S22A, S22M | S22M |
| 23 | Y23W, Y23S, Y23T, Y23A, | Y23W, Y23S | Y23W, Y23A |
| 24 | N24Q, N24D, N24E | N24Q | N24Q |
| 25 | A25I, A25V, A25L, A25M | A25I, A25V, A25L, | A25I |
| 26 | E26D, E26K, E26R, E26H, | E26D, E26K | E26D, E26R |
| 27 | L27A, L27I, L27V, L27M | L27A, L27I, L27V | L27A |
| 28 | L28I, L28V, L28A, L28M | L28I, L28V, L28A | L28A |
| 29 | V29I, V29L, V29A, V29M | V29I, V29L, V29A | |
| 30 | A30I, A30L, A30V, A30M. A30C | A30I, A30L, A30V | |
| 31 | L31I, L31V, L31A, L31M, L31C | L31I, L31V, L31A, L31M | |
| 32 | E32D, E32Q, E32N | E32D | |
| 33 | N33Q, N33E, N33D | N33Q | |
| 34 | Q34G, Q34N, Q34E, Q34D, Q34T, Q34S | Q34G, Q34N, Q34E, Q34D | |
| 35 | H35K, H35R, H35N, H35Q | H35K, H35R | |
| 36 | T36S, T36G, | T36S | |
| 37 | I37L, I37V, I37A, I27M, I37C | I37L, I37V, I37A | |

TABLE 1-continued

Substitutions in SEQ ID NO: 2.

| Position | Preferred Substitutions | More Preferred Substitutions | Alternative Preferred Substitutions |
|---|---|---|---|
| 38 | D38E, D38N, D38Q | D38E | |
| 39 | L39F, L39I, L39V, L39M, L39C, L39A, L39E, L39D, L39N, L39Q | L39F, L39I, L39V, L39M, L39A, L39E, L39D | |
| 40 | T40H, T40R, T40K, T40S, T40G, T40A, T40M, | T40H, T40S, T40G, T40A, T40M | |
| 41 | D41E, D41N, D41Q | D41E | |
| 42 | S42G, S42T, S42I, S42L, S42V, S42A, S42M, S42C | S42G, S42T, S42I, S42L, S42V, S42A | |

In certain preferred embodiments, the peptide of the invention is a peptide consisting of at least 8 consecutive amino acid residues of any of the sequences shown in Table 2 (SEQ ID NO: 3-13), which represent portions of the FIR of a wild-type influenza A hemagglutinin 2 (HA2) or influenza B hemagglutinin (HB) protein. In other preferred embodiments, the peptide consists of at least 8 consecutive amino acid residues of a variant of any one of SEQ ID NO: 3-13. In this alternative embodiment, the variant differs from the selected sequence by one or more amino acid substitutions, preferably conservative substitutions, and preferably selected from the corresponding substitution residues at each position of the peptide as are shown in Table 1.

In addition, the sequences shown in FIG. 2 and in FIG. 4 indicate a number of residues in boldface type, which represent consensus residues at the indicated positions of the aligned hemagglutinin 2 amino acid sequences. As used herein, the term "consensus" as applied to an amino acid residue in alignment comparison of amino acid sequences refers to an amino acid that appears in a majority of the aligned sequences at a given position. In FIG. 2, the consensus residues are those amino acids that appear at a given position in at least seven of the thirteen sequences shown in the figure. In FIG. 4, the consensus residues are those amino acids that appear at a given position in at least eight of the fourteen sequences shown in the figure. In the region of residues 72 to 113 of the hemagglutinin 2 sequences compared in FIG. 4, the consensus residues are: V73, E74, R76, I77, L80, D86, D90, W92, S93, Y94, N95, A96, E97, L98, L99, V100, L101, L102, E103, N104, T107, D109, D112, and S113. Preferably, the peptides of the invention, including any of the embodiments described herein, include one or more of these consensus residues, up to and including all of the consensus residues within the region of the HA2 protein or variant thereof encompassed by the peptide.

TABLE 2

| Peptide Sequence | Sequence Identifier | HA or HB variant |
|---|---|---|
| VEDTKIDLWSYNAELL | SEQ ID NO: 3 | residues 84-99 of A/H3, A/H4 and A/H14 |
| VDDGFLDIWTYNAELLVLL | SEQ ID NO: 4 | residues 84-102 of A/H1 |
| MEDGFLDVWTYNAELL | SEQ ID NO: 5 | residues 84-99 of A/H5 |
| TRDSMTEVWSYNAELL | SEQ ID NO: 6 | residues 84-99 of A/H7 |
| VDDQIQDIWAYNAELL | SEQ ID NO: 7 | residues 84-99 of A/H9 |
| VDDLRADTISSQIELA | SEQ ID NO: 8 | residues 84-99 of HB |
| MEDGFLDVWTYNAELL | SEQ ID NO: 9 | residues 84-99 of A/H2 and A/H6 |
| TKDSITDIWTYNAELL | SEQ ID NO: 10 | residues 84-99 of A/H10 |
| IDDAVTDIWSYNAKLL | SEQ ID NO: 11 | residues 84-99 of A/H13 |
| TRDSLTEIWSYNAELL | SEQ ID NO: 12 | residues 84-99 of A/H15 |
| VDDAVTDIWSYNAKLL | SEQ ID NO: 13 | residues 84-99 of A/H16 |

All of the sequences in Table 2 except influenza B hemagglutinin 2 peptide (SEQ ID NO: 8) share greater than 50 percent sequence identity with SEQ ID NO: 3, i.e., SEQ ID NO: 4, 5, 9, and 13 are 62.5 percent identical to SEQ ID NO: 3, and SEQ ID NO: 6, 7, 9, 10, 11 and 12 are 56.2 percent identical to SEQ ID NO: 3. The influenza B hemagglutinin 2 shares about 31 percent sequence identity with SEQ ID NO: 3, however the differences between SEQ ID NO: 8 and SEQ ID NO: 3 are predominately conservative substitutions. In addition, each of the peptides represented by SEQ ID NO: 3-13 includes one or more of consensus residues D86, D90, W92, S93, Y94, N95, A96, E97, L98, L99, V100, L101, and L102.

In another aspect, the present invention provides analogs of a peptide of the invention. In one embodiment, the analog comprises a cyclic peptide containing at least two cysteine residues sharing a disulfide linkage (i.e., a cystine bridge) to form a cyclic structure. Each cysteine residue is independently a residue of peptide, a residue bound of the amino-terminus of the peptide, either directly or though a linking peptide sequence, or a residue bound to the carboxy-terminus of the peptide, either directly or through a linking peptide sequence. Cyclic peptide structures are known to improve the in vivo biostability of many peptides.

In another embodiment, the analog comprises at least one non-natural amino acid residue (e.g., a D-amino acid residue, an N-methylated residue such as N-methyl valine, hydroxyproline, aminobutyric acid, and the like). Certain of such substitutions of non-natural amino acids are known to impart resistance to cleavage by peptidases in many peptide compounds (e.g., D-amino acids, hydroxyproline) or increase alpha-helical content of the peptide (e.g., aminobutyric acid).

In yet another embodiment, the analog can include one or more natural amino acid substitutions of an amino acid residue of the peptide with one or more proline, glycine, or glutamic acid residues. Proline and glycine residues can disrupt the alpha-helical content of a peptide, if needed or desired, while glutamic acid residues can increase alpha-helical content of the peptide.

In still another aspect, the present invention provides a derivative of a peptide or an analog of the invention in which the peptide or analog includes an appended group. In one embodiment, the appended group is a lipid, such as a $C_8$ to $C_{20}$ alkyl group or alkyl carboxylate group bound to the peptide via an ester, amide, ether, thioester, or thioether bond. For example, the derivative can include a fatty alkyl ester group, such as a myristate group bound to a residue of the peptide. Lipid substituents can increase the biostability of peptide, for example.

In another embodiment, the derivative comprises a polyethylene glycol (PEG) group appended to an amino, hydroxyl, or thiol substituent on a side chain of one or more of the amino acid residues of the peptide. Such PEG derivatives can often improve protein pharmacokinetics, e.g., by inhibiting uptake in organs such as the liver, which include significant levels of peptidases.

In yet another derivative embodiment, the peptide includes a non-HA2 polypeptide sequence bound to the amino terminus of the 8 to 40 amino acid peptide, the carboxy-terminus of the peptide, or both termini. The non-HA2 sequence can be a non-HA2 protein (e.g., serum albumin) or a portion of a non-HA2 protein, or can comprise, for example, a sequence to aid in solubilizing the peptide, such as ASKSKSK (SEQ ID NO: 15) or a variant thereof, preferably added to the carboxy-terminus of the peptide.

Another preferred derivative of the invention is an isolated polypeptide comprising a first peptide segment consisting of a peptide of the invention (e.g., 8 to 40 consecutive amino acid residues of a portion of a wild-type influenza HA2 protein from the region of residues 72 to 113 of the wild-type sequence or a variant thereof), and at least one additional peptide segment comprising a non-HA2 peptide sequence bound to the amino-terminus, the carboxy-terminus, or to both the amino- and carboxy-termini of the first peptide segment.

In another aspect, the present invention provides an isolated antibody that is specific for (i.e., is capable of specifically and selectively binding to) a peptide, analog, or derivative of the invention. Such antibodies are useful as reagents to determine the presence of concentration of the peptide, analog, or derivative of the invention in a biological sample from a subject that has been treated with a composition of the invention. In addition, antibodies that target peptides of the invention that comprise portions of wild-type hemagglutinin 2 subtypes can also bind to the natural hemagglutinin 2 proteins. Such binding can provide some level of inhibition of the influenza virus-cell fusion process, as well. Preferably, the antibody is a monoclonal antibody, which may be a chimeric or humanized antibody derived from an antibody of a non-human animal such as a mouse. Methods of preparing monoclonal antibodies from a given protein or peptide are well known in the art. Methods of preparing chimeric or humanized antibodies are also well known to the person of ordinary skill in the art.

Another aspect of the invention is a pharmaceutical composition comprising a peptide, analog, derivative, or antibody of the invention that can be used in a method of treating or preventing an influenza infection. In certain preferred embodiments, this composition includes the peptide, analog, derivative, or antibody of the invention in a pharmaceutically acceptable vehicle or carrier suitable for delivery of the peptide, analog, derivative or antibody to a subject, e.g., to the nasal passage or pulmonary tract. Vehicles and carriers suitable for delivering an active ingredient to the nasal passage or pulmonary tract are well known in the art and include saline solutions, buffered saline solutions, inhalable powders, and the like. The carrier can also include other excipient ingredients, such as surfactants, preservatives, dispersants, and the like. The compositions can be delivered as an aerosol, as a non-aerosolized liquid, an ointment or cream (e.g., for nasal application), and the like. The pharmaceutical composition of the invention can be used as part of a method to treat or prevent an influenza infection by administering to a subject suffering from influenza an influenza inhibiting amount of the pharmaceutical composition of the invention.

Another aspect of the invention is the use of a peptide, analog, derivative, antibody or pharmaceutical composition of the invention to treat or prevent an influenza infection. This can include the use of the peptide, analog, derivative or antibody of the invention to prepare a medicament for treating influenza.

Influenza Viruses.

There are multiple subtypes of the influenza A virus. Each viral subtype comprises one specific combination of versions of two glycoproteins that are embedded in the lipid membrane envelopes of the viruses. The two subtype-defining glycoproteins are hemagglutinin 2 (HA2) and neuraminidase. There are sixteen known variants of HA2, which are referred to as H1 through H16, respectively, and nine known variants of neuraminidase, which are referred to as N1 through N9, respectively. Each viral subtype is specified characterized by its hemagglutinin 2 and neuramimidase variant numbers. For example, influenza A subtype H3N2 is a swine flu, and subtype H5N1 is an avian flu.

HA2 is the fusion protein of all of the viruses in the orthomyxovirus family, which includes the influenza viruses. The FIR of every influenza virus lies within its HA2 glycoprotein. The amino acid sequences of thirteen of the sixteen known HA2 variants, H1, H2, H3, H4, H5, H6, H7, H8, H9, H10, H11, H12, H13, H14, H15, and H16, are shown in FIG. 2 (SEQ ID NO: 17, 18, 19, 20, 21, 22, 23, 24, 25, 26, 27, 28, and 29, respectively). The sequences of the H8, H11, and H12 subtypes have not been reported. The fusion initiation regions of the H3 hemagglutinin 2 has now been identified as residues 77 through 119 of the H3 amino acid sequence (SEQ ID NO: 19) as shown in FIG. 2.

An isolated peptide referred to herein as flu inhibitor-3 (F3), which embodies the amino acid sequence VEDTKIDL-WSYNAELL, SEQ ID NO: 3 (residues 84-99 of SEQ ID NO: 19; H3 HA2), has now been found to have potent anti-viral properties. An isolated peptide comprising the same sixteen amino acids, in the randomly scrambled sequence SWLVNKIYLTDDEVEL (SEQ ID NO: 14), exhibits no discernable anti-viral properties. The anti-viral properties of F3 include viral binding inhibition as evidenced by hemagglutination assays. F3 also inhibits viral binding, fusion, and infection as evidenced by plaque assays.

Anti-Influenza Virus Activity.

F3 has potent infection inhibition activity against a broad range of H1, H3, H5, and influenza B viruses, which display significant diversity in both the overall sequence and structure of their respective HA2 proteins. The broad spectrum of activity of F3 may be related, at least in part, to the fact that the FIR, and particularly the portion of thr FIR represented by residues 84-99 of all known influenza A subtypes and of influenza B, is one of the most highly conserved regions in the HA2 protein. While not wishing to be bound by theory, it is believed that the sequence similarity between F3 and the corresponding region (residues 84-99) of wild-type HA2 subtypes allows the peptide to effectively bind to or otherwise interact with the corresponding portion of the FIR across HA subtypes. This interaction interferes with the normal operation of the HA protein during the fusion process (e.g., by interfering with protein aggregation or conformation changes necessary for the fusion process to proceed).

F3 has been synthesized in gram quantities on PEG-PS-PAL resin using standard FMOC chemistry. The bulk peptide product has been purified using HPLC to >95% with residual material principally being shorter related peptides. The purified peptide was lyophilized to remove solvent. The lyophilized powder can be further processed, for example, by dissolving it in hexafluoroisopropanol and evaporating the solvent with the aid of a stream of ultrapure nitrogen (Praxair UHP, 99.999%). The resulting powder can then be reconstituted at a later time by dissolving the powder in an aqueous buffer, such as 10 mM potassium phosphate or phosphate buffered saline (PBS). The concentration of F3 in solution can be determined using the formula: mg/ml=(A280×mw)/e, where e represents the sum of the molecular extinction coefficient of the two chromogenic amino acids in the peptide amino acid sequence at 280 nm, i.e., the sum of 5560 (Trp)+ 1200 (Tyr), to provide e=6760.

F3 has potent and broad-based influenza A virus inhibitory activity and exhibits picomolar inhibition in plaque reduction assays. Using an immunoplaque assay with AVICEL® microcrystalline cellulose as the overlay (Matrosovich et al., 2006), plaques are detected by fixing the monolayers and staining with a specific antibody to the influenza virus nucleoprotein. In the peptide inhibition assay, peptide is preincubated with about 100 plaque forming units (pfu) of the virus for approximately 1 hour, then used to infect the monolayers. Two conditions were used for the incubation: (1) standard condition in which the peptide is included in the overlay at the same concentration that was used in the preincubation step, or (2) a condition in which the peptide is not included in the overlay.

F3 was evaluated for inhibition of multiple subtypes of influenza A viruses utilizing Madin-Darby Canine Kidney ("MDCK") cell plaque assays performed using the A/WSN/33 (H1N1) and A/Udorn/72 (H3N2) subtypes of influenza A virus. Dilutions of 50 μM to 2.5 μM of F3 and the randomly scrambled control peptide (SEQ ID NO: 14) were used to evaluate the effects of these peptides on viral infectivity. Six dilutions of F3 and of the control peptide were tested against the H1N1 viral subtype; and another six dilutions of each peptide were tested against the H3N2 viral subtype.

Under condition (1), F3 inhibited normal sized plaque formation by several different stains of H1N1 and H3N2 influenza A virus with $IC_{50}$ of in the range of about 100-500 picomolar (pM). Under condition (2) the $IC_{50}$ for inhibition of normal sized plaques was in the range of about 10 to 100 nanomolar (nM) for F3. At low nM concentrations (<10 nM) for condition (1), or low μM (<10 μM) for condition (2), the presence of "mini-plaques" were apparent.

The scrambled control peptide did not inhibit influenza A virus plaque formation under any condition, indicating that the amino acid sequence of the peptide is important and that non-specific effects cannot account for the inhibition.

F3 also is active against a recombinant H5N1 influenza virus and against two strains of influenza B (B/Shanghai/361/2002 and B/Shanghai/10/2003), in vitro, in immunoplaque assays with $IC_{50}$ in the low mM range (<5 nM). Given the diversity of these different influenza A and B strains, F3 is likely to be effective against most influenza viruses.

Using methods taught in U.S. patent application Ser. No. 10/578,013, the FIR of the H1 subtype influenza A viruses has now been identified as residues 77 through 110 of the H1 HA2 sequence (SEQ ID NO: 17). An isolated peptide having the amino acid sequence of SEQ ID NO: 4, designated herein as flu inhibitor-1 (F1) also has potent (picomolar) antiviral activity against both the H1 and H3 influenza A virus subtypes in plaque assays. The amino acid sequence of F1 matches residues 84-102 of the H1 FIR sequence, SEQ ID NO: 17.

Studies have been conducted with various influenza strains to better understand the mechanism of action of the peptides of the invention, e.g., to determine which step in the viral replication cycle is inhibited by F3, F1, and related influenza virus inhibitory peptides. At optimal numbers of red blood cells and concentrations of influenza A/PR/8/34 (H1N1), both F3 and F1 inhibited influenza virus-induced hemagglutination at about 10 μM concentrations. At optimal cell and virus dilutions (1:8 for both), F3 inhibited hemagglutination at concentrations between 12.5 and 6.25 μM. Similar results were obtained with other H3 and H1 strains, i.e., H1N1 strains A/New Calcdonia/20/99 and A/WSN/33; and H3N2 strains A/California/07/2004, A/New York/55/04, and A/Udorn/72. In contrast, a control peptide having the amino acid sequence of SEQ ID NO: 14, a scrambled version of F3, did not inhibit hemagglutination at any concentration.

Higher concentrations of virus can overcome the hemagglutination inhibition, suggesting a stochastic mechanism. The result with this traditional virus-to-cell binding assay suggests that the peptides of the invention interact directly with virions to inhibit binding to cells. In contrast, the FUZEON® anti-HIV drug interacts with a short-lived fusion intermediate and not with a virion structure (Debnath, 2006; Platt, Durnin, and Kabat, 2005). The direct interaction with native virion structures may account, at least in part, for the very high potency of F3 and F1 (about 200 pM for normal-sized plaques) relative to FUZEON® anti-HIV drug (4 to 280 nM depending of the HIV-1 strain) in virus infectivity assays. The mini-plaques discussed above may have resulted from refolding of HA on the virion.

Refolding of HA has been previously suggested to occur after exposure to a small molecule inhibitor of influenza A virus known to interact with HA (Cianci et al., 1999; Luo, Colonno, and Krystal, 1996; Luo et al., 1997). This entry inhibitor and others (Hoffman et al., 1997) were quite significant advances in the late 1990's, as they identified HA as an important therapeutic target. However, such small molecule inhibitors have not to date been developed as influenza drugs, most likely due to their relatively low efficacy, with $IC_{50}$ in the low to mid μM concentration range. An evolving consensus in the burgeoning field of viral entry inhibitors is that small molecule drugs may not be able to effectively interfere with the extensive protein structural transitions and multiple intramolecular interactions that HA and other viral fusion proteins undergo during the viral entry process.

A working model for the process of influenza virus virion-cell fusion can be extrapolated from intense work on influenza virus and other RNA viruses over many decades. A schematic representation of such a model is shown in FIG. 5. While still hypothetical in some aspects, this model can highlight the importance of structural/functional motifs of the influenza A virus glycoproteins that can serve as drug development targets. In FIG. 5, Panel A shows binding of the influenza hemagglutinin 1 (HA1) protein to the cell receptor, which consists of sialolipids or sialoproteins. Panel B shows entry of the influenza virion into the endocytic vesicle. An influenza virus protein known as M2 viroporin lowers the pH to trigger rearrangement of the helical domains of the HA2 protein. The sequence of the HA2 protein corresponding to the amino acid sequence of F3 (SEQ ID NO: 3) is located next to a metastable "spring" sequence. The rearrangement allows the fusion peptide portion of the HA2 protein to interact with the vesicle membrane. Panels C and D illustrate HA2 "snapping back" by a "leash-in groove" mechanism, bringing the viral and cell membranes into closer proximity. For clarity, HA1 and the sialoreceptors are not shown in Panels C-E. Panel C' shows an alternative mechanism in which sequences of HA2, which form a track with the ability to interface with bilayer membranes, may facilitate mixing of cellular and viral membranes. Panel E shows the formation of the "fusion pore" and entry of ribonuceloprotein segments from the virus into the cell.

Live Animal Studies.

The ferret is generally considered the best model for influenza virus infection of humans (Govorkova et al., 2005; Hampson, 2006; Maher and DeStefano, 2004; van Riel et al., 2007). Indeed, European Union guidance for influenza vaccine efficacy specifically requires testing in the ferret model. Mice and other small mammals can be infected with human strains of influenza A viruses, but this typically requires, in the case of seasonal strains, adaptation of the virus for the new host. In contrast, ferrets can be infected with most strains of human influenza A viruses without adaptation. The tissue distribution and pathogenesis of adapted influenza A viruses in mice is distinct from that which occurs in human disease (Lu et al., 1999). The pathogenesis of influenza A virus infection in ferrets is very similar to that observed in humans. When ferrets are experimentally inoculated intranasally, local replication of the virus in the upper respiratory tract occurs. The distribution of sialic acid receptors in the respiratory tract of ferrets is similar to humans (van Riel et al., 2006; Yen et al., 2007).

In a manner strikingly similar to humans with the flu, ferrets develop decreased activity, fever, inappetence, nasal discharge, sneezing, dyspnea, diarrhea, conjunctival discharge, and neurologic signs. The predominant pathological finding in both ferrets and humans is desquamation of ciliated respiratory epithelium and infiltration of the submucosa of the nasal cavity with infiltrating inflammatory cells. Within 48 hours after the infection of a ferret by the influenza virus, nearly complete destruction of the nasal respiratory epithelium occurs, leaving only the basement membrane.

The major distinction between influenza in ferrets and humans is the length of time that symptoms of the disease are displayed. Ferrets begins to develop symptoms of influenza sooner than one day after infection, but by 4 days after infection have resolved most of the well known findings (decreased activity, fever, inappetence, nasal discharge, sneezing, etc.). It should be noted that many strains of human influenza A virus are capable of infecting the lower respiratory tract of ferrets to varying degrees. As in humans, highly pathogenic strains of influenza A virus are capable of spreading in ferrets from either the upper respiratory tract to the brain or from the lower respiratory tract to the circulation and other organs. Current H5N1 strains of avian influenza A virus can establish fatal infections in ferrets (Govorkova et al., 2005; Thiry et al., 2007; Vahlenkamp and Harder, 2006).

Initial in vitro studies focused on well-characterized laboratory strains of influenza A virus corresponding to subtypes currently circulating in humans including, A/WSN/33 (H1N1), A/PR/8134 (H1N1) and A/Udorn/72 (H3N2). Peptides F3 and F1 showed similar efficacy in plaque reduction assays against several other strains of influenza A virus, including clinical isolates of H1N1 (A/New Calcdonia/20/99) and H3N2 (A/NY/55/04; A/Cal/07/04) strains, which have not been extensively evaluated in the laboratory. Studies with recent clinical isolates such as these are important to establish the efficacy of the therapeutics with viruses currently causing influenza in humans. Importantly, these strains also caused influenza in ferrets growing to high titers in the nasal turbinates and lungs of this species after intranasal inoculation.

For all studies, virus isolates were propagated in embryonated chicken eggs (obtained from Charles River Laboratories or Louisiana State University Poultry Sciences Department) using standard procedures. Allantoic fluids were harvested from 11 day old eggs one day after inoculation, and virus pools were examined for hemagglutination activity against turkey red blood cells (tRBC) (Lampire Laboratories, USA) using standard procedures. Positive hemagglutination (>256 HA units) pools were titrated by viral plaque assay as described above and stored in liquid nitrogen until used for challenge studies. The peptides were prepared in phosphate buffer and the buffered solutions were applied directly to the nasal passages of anaesthetized ferrets using a pipette (intranasal administration route).

Challenge Study 1.

Ferrets were pretreated with F3 or with a scrambled control version of the peptide (SEQ ID NO: 14), for two days prior to virus exposure (Day-2 and Day-1) at a dose of about 0.3 mg/Kg by the intranasal route, either once a day or twice a day. Twelve hours after the last treatment, the animals were infected by intranasal inoculation with about 105 pfu of the H3N2 influenza A/Cal/07/04 strain, which is at least 100 times the minimum infectious dose as determined in infectious dose finding studies. The peptides were readministered to the ferrets at the 0.3 mg/Kg dose about 12 hours later on Day 0, as well as on Day 1 and Day 2 after viral exposure. On Day 2, all ferrets treated with the scrambled control peptide had developed significant respiratory distress (rapid shallow breathing), high fever and sneezing. In contrast, none of the animals treated with F3 had severe respiratory distress, although a subset (2/5in the twice a day pre-dosing group, 1/6in the once a day pre-dosing group) showed some very mild respiratory signs with slight fever. On Day 3, all ferrets treated with F3 showed no clinical signs of influenza, while 50% of the ferrets treated with the scrambled control peptide still presented with lethargy, and 100% of scrambled control peptide-treated ferrets displayed significant nasal discharge. Clearly, F3 provided a significant and surprisingly effective treatment benefit in this initial challenge experiment.

Challenge Study 2.

Figure 6C:
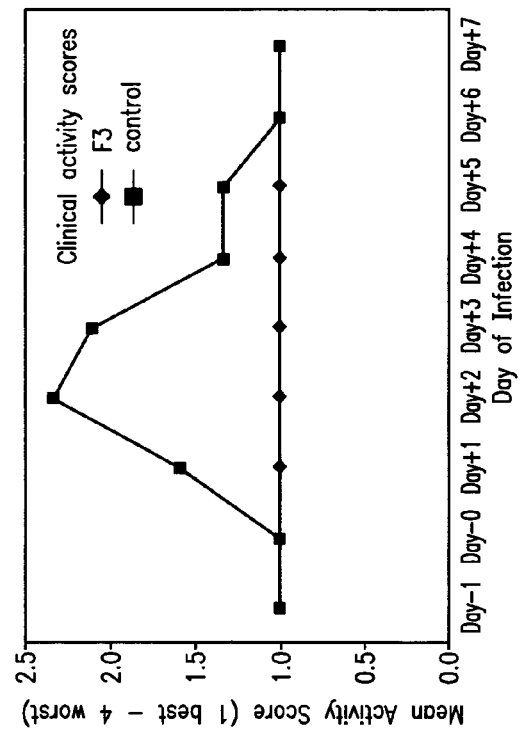
FIG. 6 shows pathological responses observed for two groups of ferrets challenged with influenza virus A/Cal/07/04 and treated with a peptide of the invention or a control peptide.
Figure 6A:
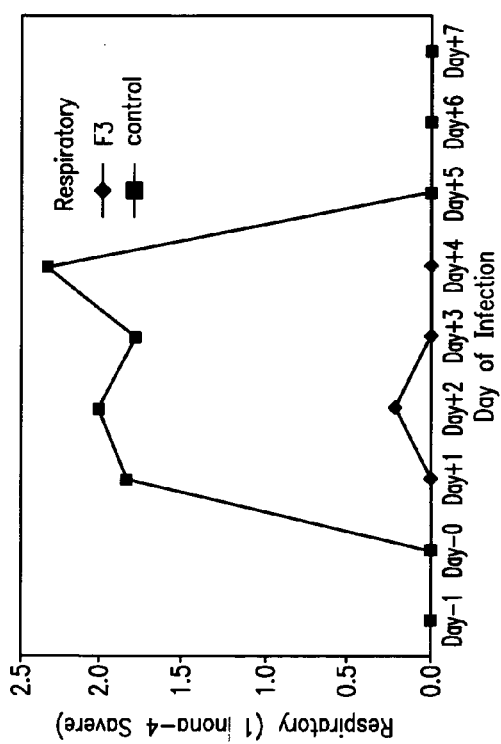
Figure 6B:
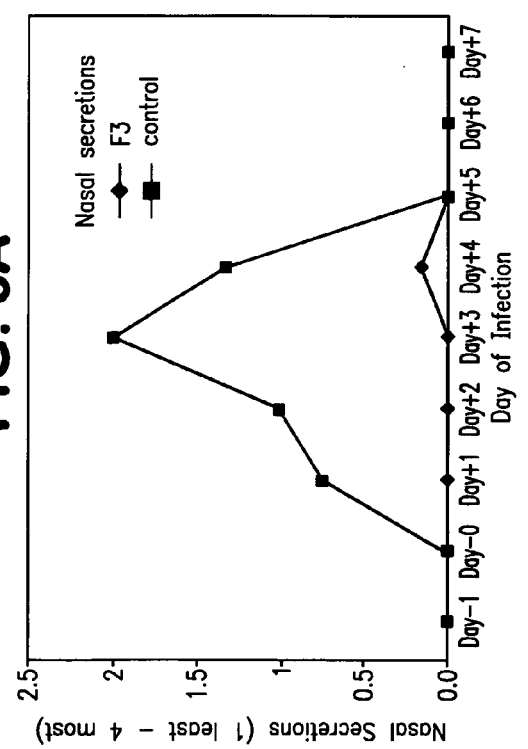

In a second challenge study, 12 ferrets were included in the F3 treatment group and 12 ferrets were included in the control peptide group. The animals were infected with about 105 pfu of influenza A/Cal/07/04; however, in this study the ferrets were treated with 0.3 mg/Kg of F3 or control peptide four hours after viral exposure on Day 0, with no pre-viral exposure treatments. On Day 2, all 12 ferrets that were treated with the scrambled control peptide had developed significant respiratory distress, high fever, and sneezing. In contrast, none of the animals treated with F3 had any signs of respiratory distress or other signs of influenza at this time. FIG. 6 shows the pathological responses observed in the ferrets during the study, obtained by monitoring of respiratory distress (Panel A), nasal discharge (Panel B), and activity (Panel C) for both treatment groups over the in life study period.

As indicated in FIG. 6, the F3-treated animals showed significantly reduced pathological responses relative to the control group. Only two animals of the F3-treated group developed mild signs of influenza and this occurred on Day 4 of the experiment, two days after treatment with the peptide had been stopped. In addition to clinical parameters, nasal aspirates and pulmonary and extrapulmonary tissues were harvested at daily intervals throughout the study period for virus titer, gross pathology, and histopathologic analysis. Animals that were treated with F3 showed normal lung presentations. In contrast, ferrets treated with the control peptide showed evidence of inflammation. Tissues from F3-treated ferrets showed markedly reduced pathology compared to control peptide-treated animals, with the control peptide-treated ferrets showing infiltrations, bronchial inflammation, with bronchial exudates characteristic of an influenza infection.

Figure 7A:
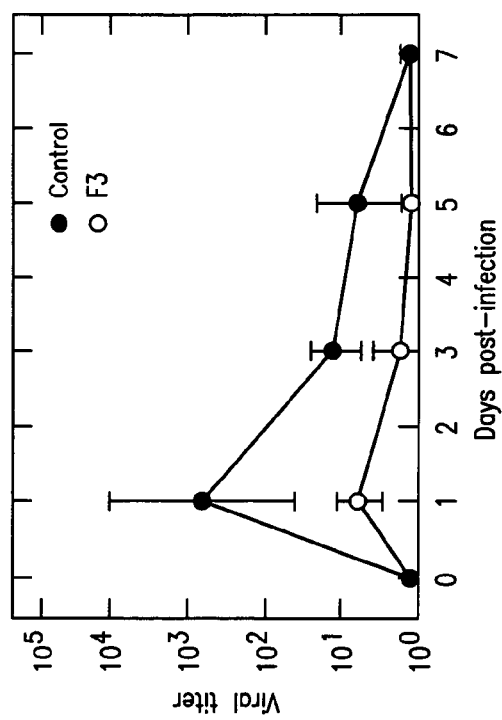
FIG. 7 shows virus titer analyses of samples from ferrets treated with a peptide of the invention or a control peptide and infected with influenza virus A/Cal/07/04.
Figure 7B:
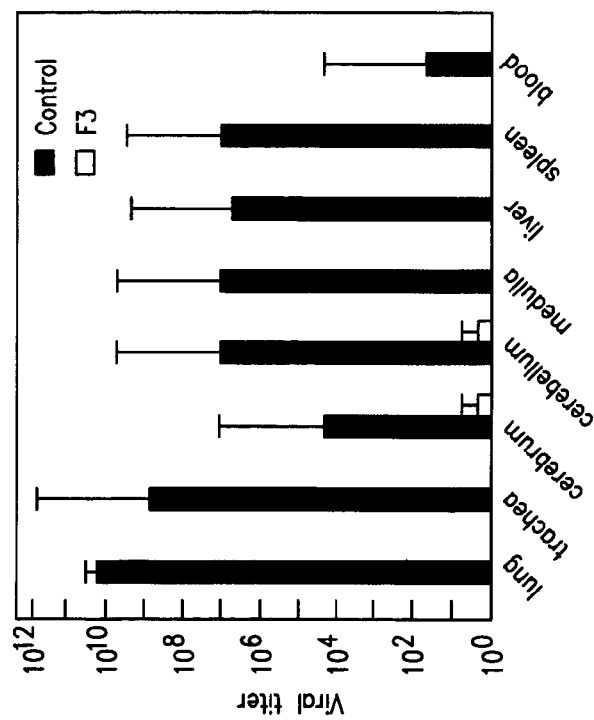
Figure 8:
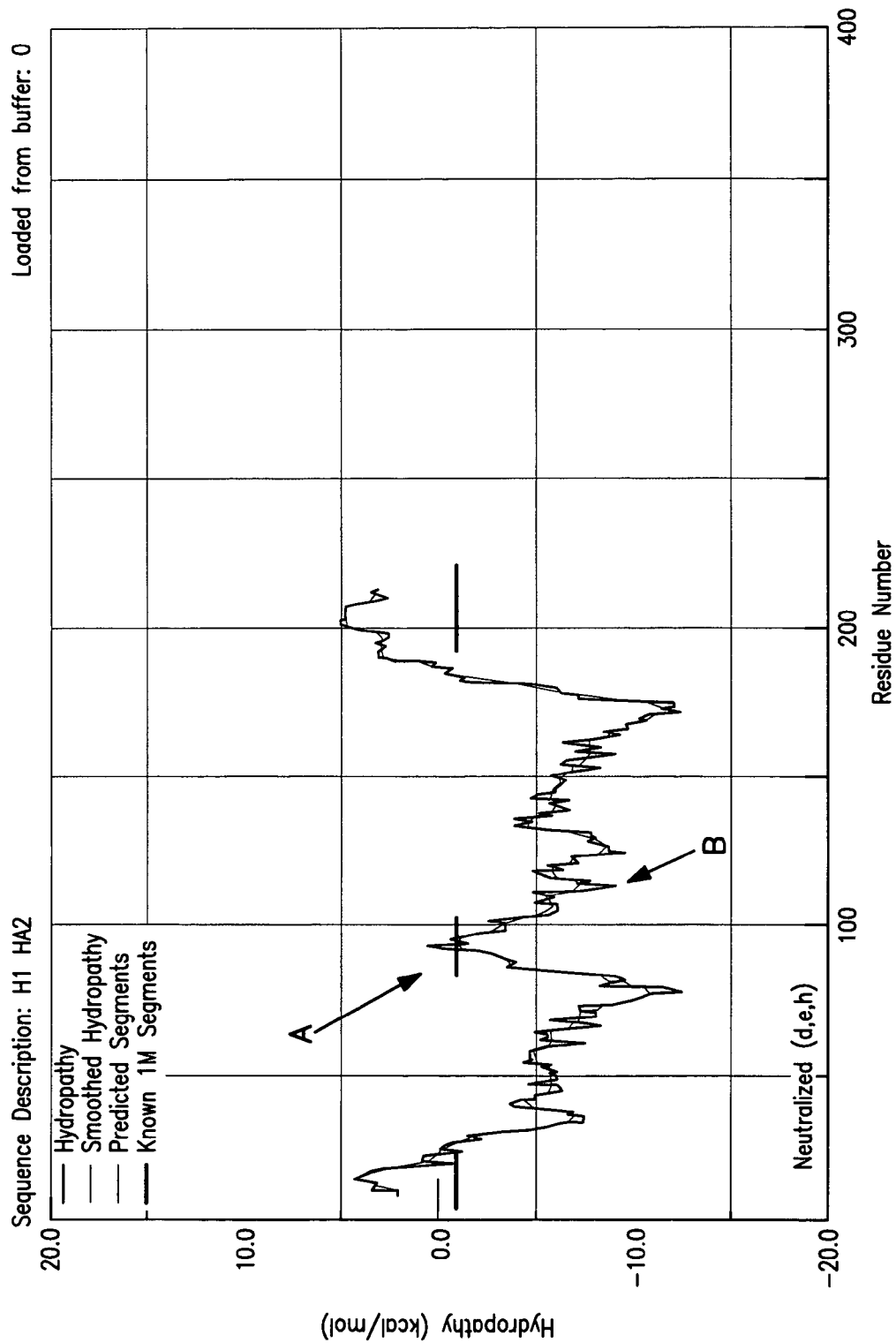
FIG. 8 shows a Wimley-White interfacial hydropathy plot for Influenza A H1 hemagglutinin 2.
Figure 9:
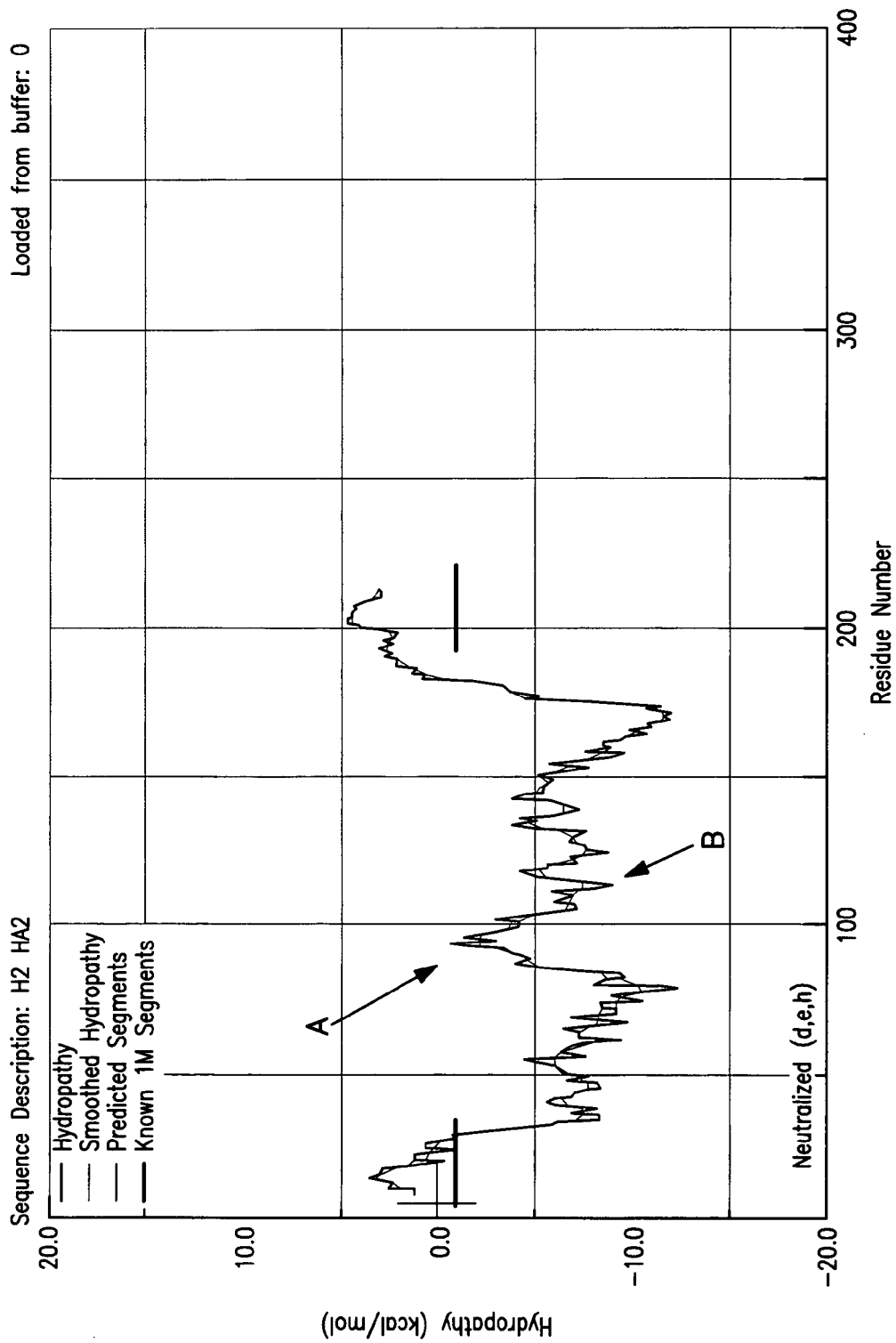
FIG. 9 shows a Wimley-White interfacial hydropathy plot for Influenza A H2 hemagglutinin 2.
Figure 10:
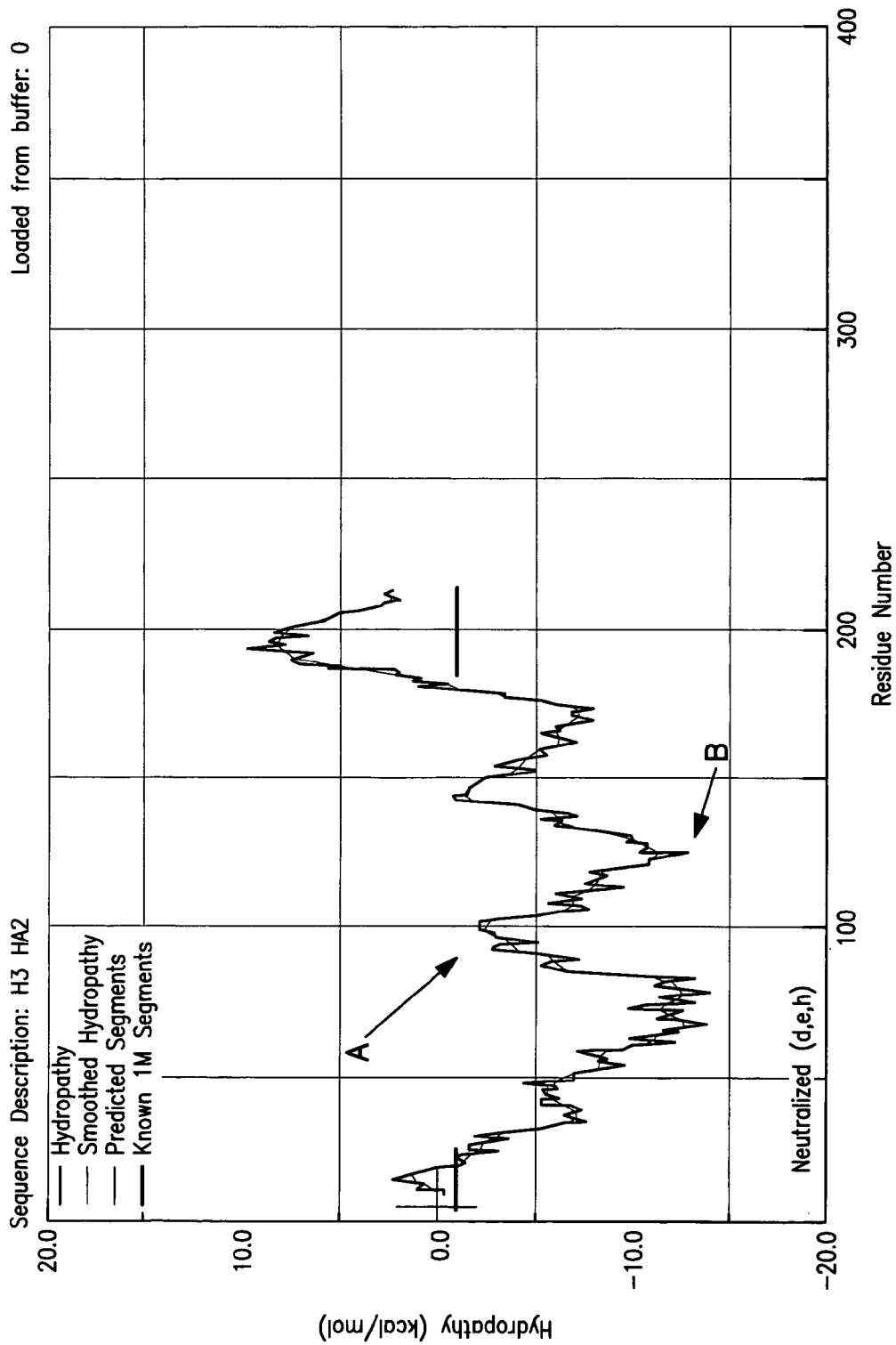
FIG. 10 shows a Wimley-White interfacial hydropathy plot for Influenza A H3 hemagglutinin 2.
Figure 11:
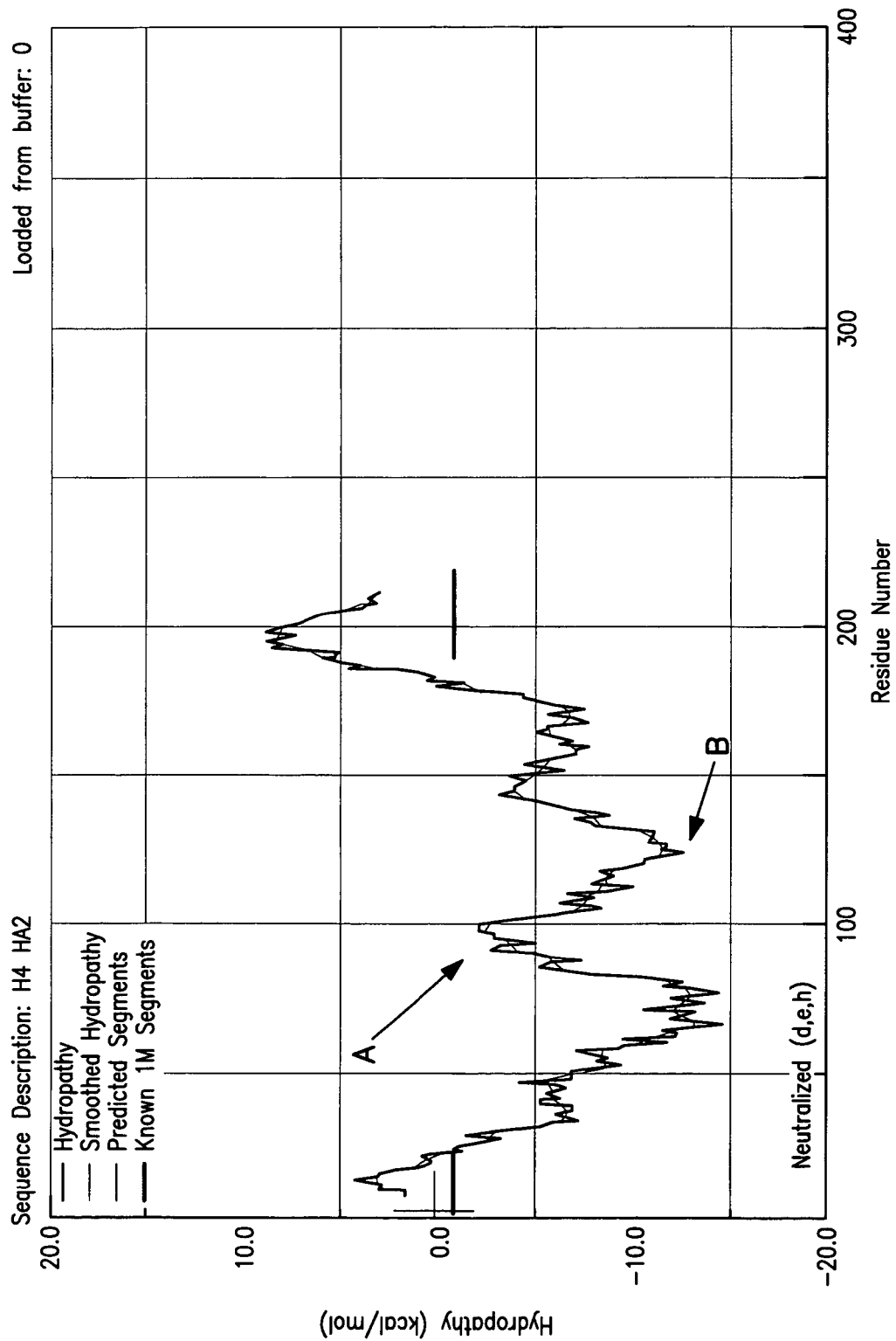
FIG. 11 shows a Wimley-White interfacial hydropathy plot for Influenza A H4 hemagglutinin 2.
Figure 12:
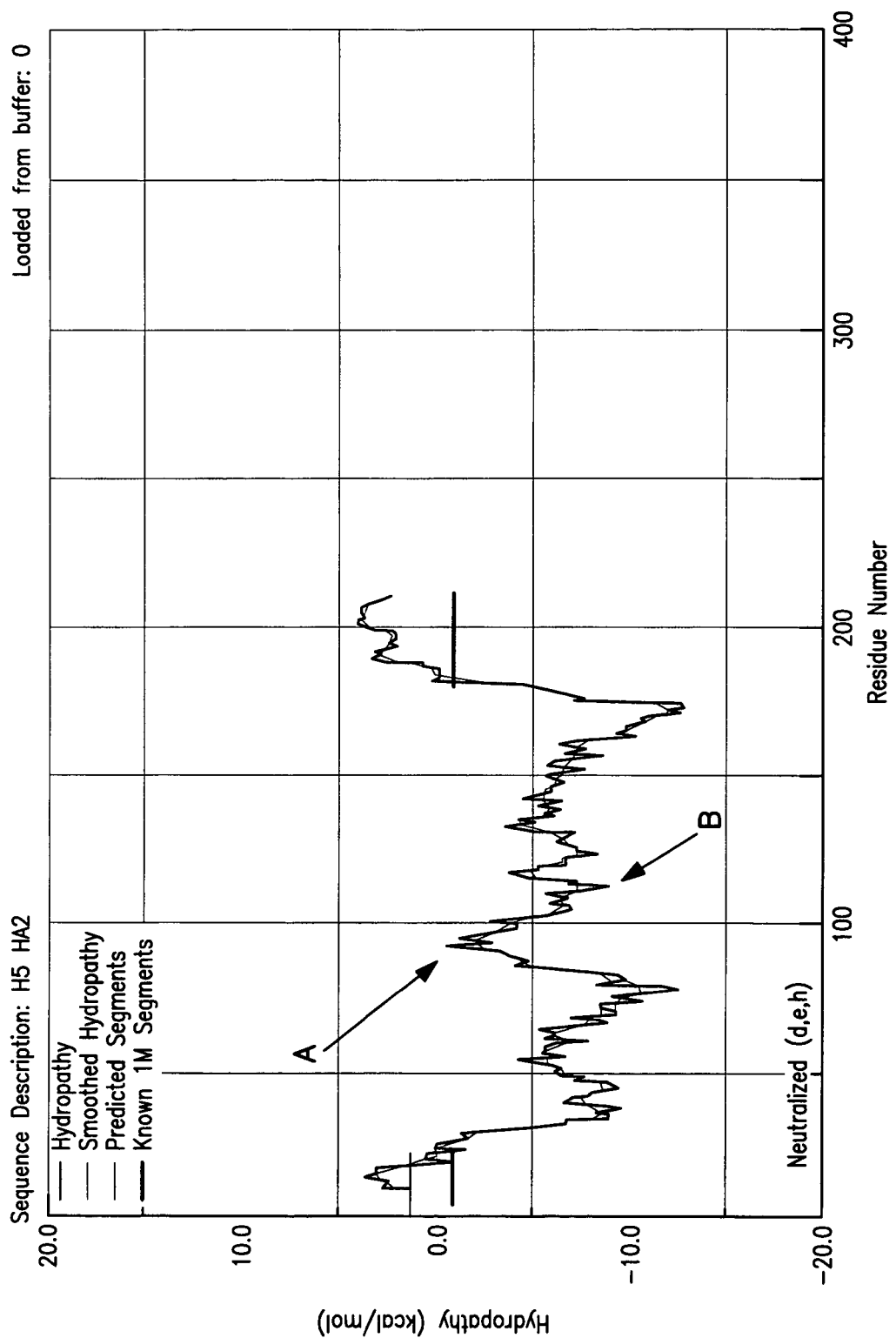
FIG. 12 shows a Wimley-White interfacial hydropathy plot for Influenza A H5 hemagglutinin 2.
Figure 13:
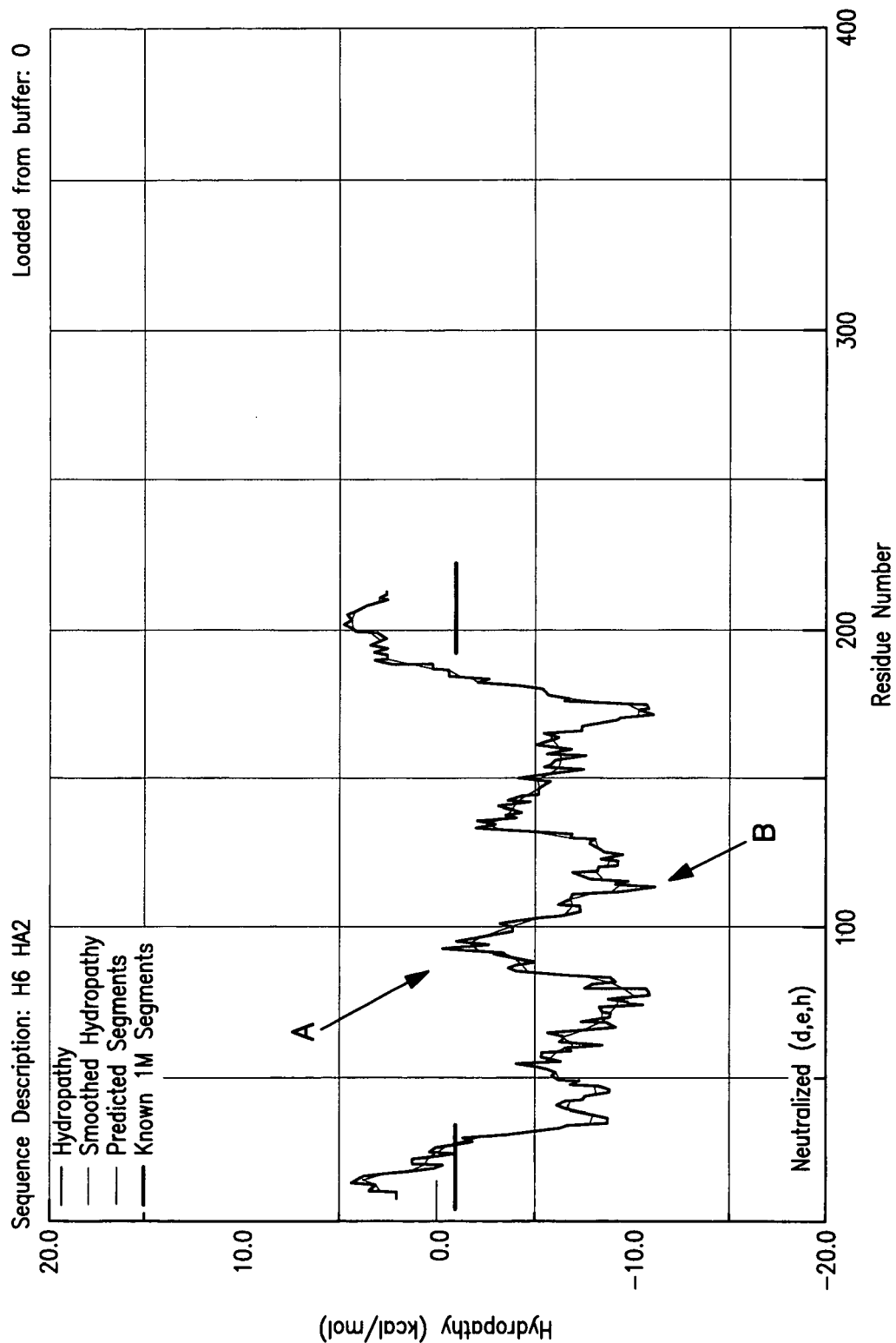
FIG. 13 shows a Wimley-White interfacial hydropathy plot for Influenza A H6 hemagglutinin 2.
Figure 15:
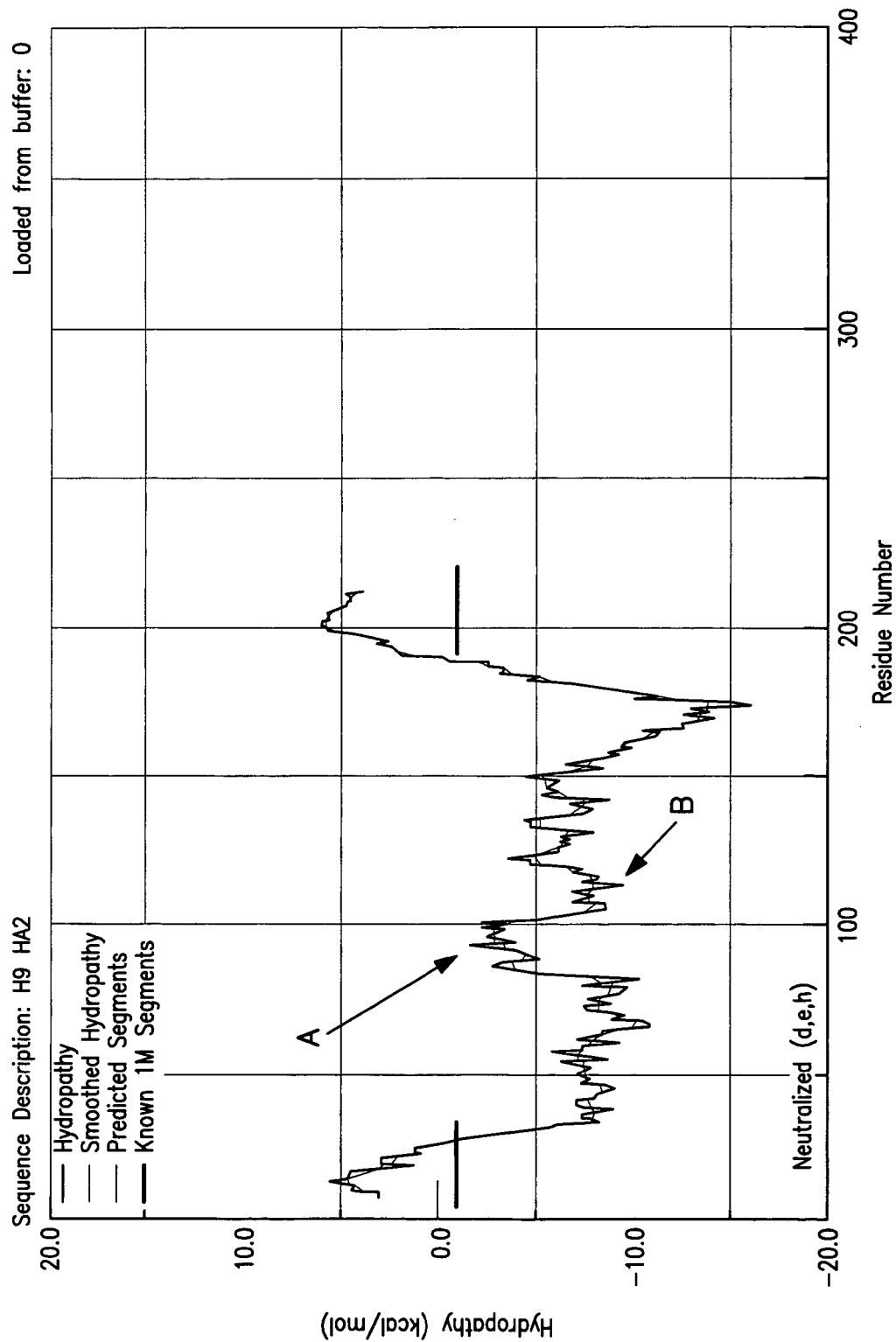
FIG. 15 shows a Wimley-White interfacial hydropathy plot for Influenza A H9 hemagglutinin 2.
Figure 16:
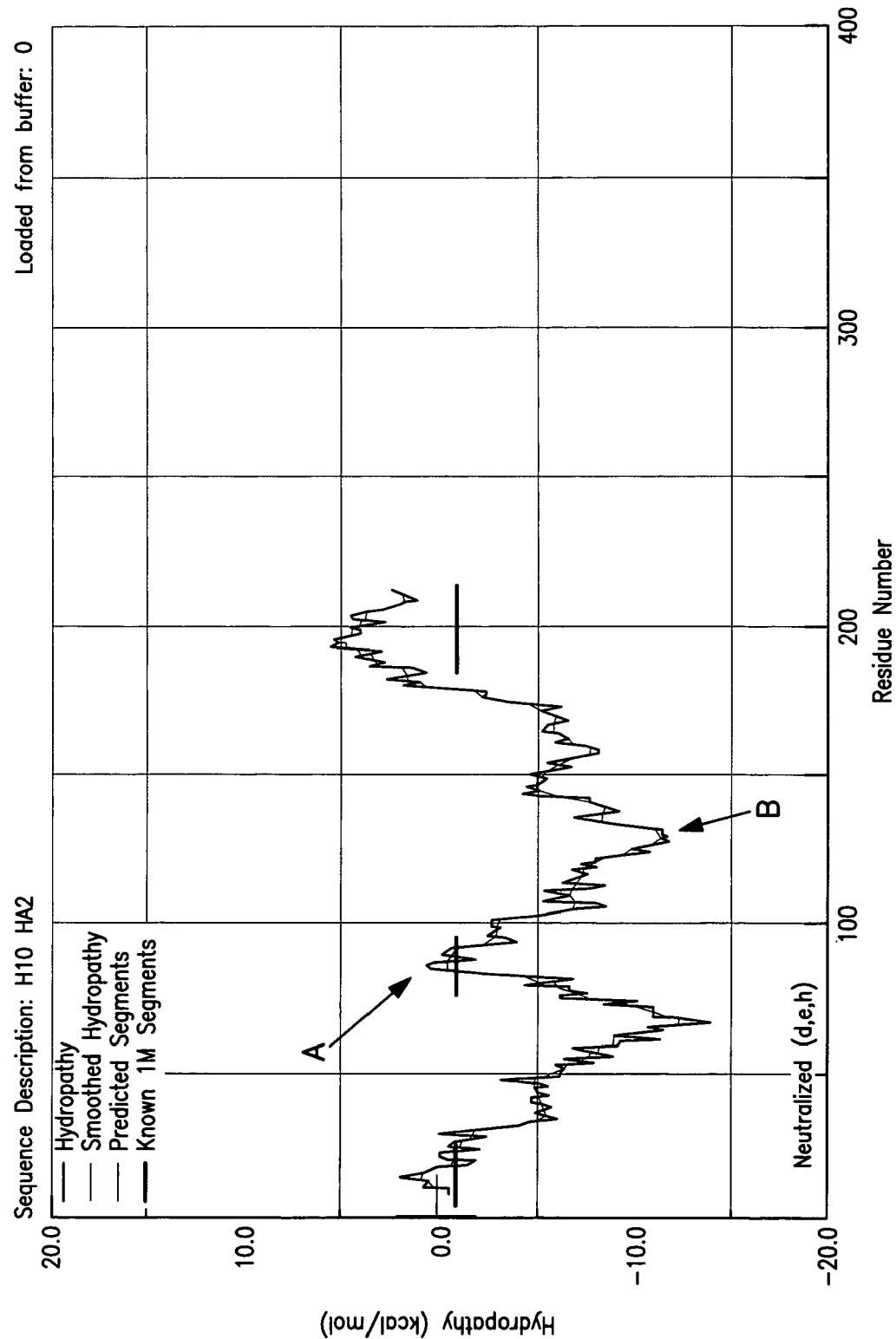
FIG. 16 shows a Wimley-White interfacial hydropathy plot for Influenza A H10 hemagglutinin 2.
Figure 17:
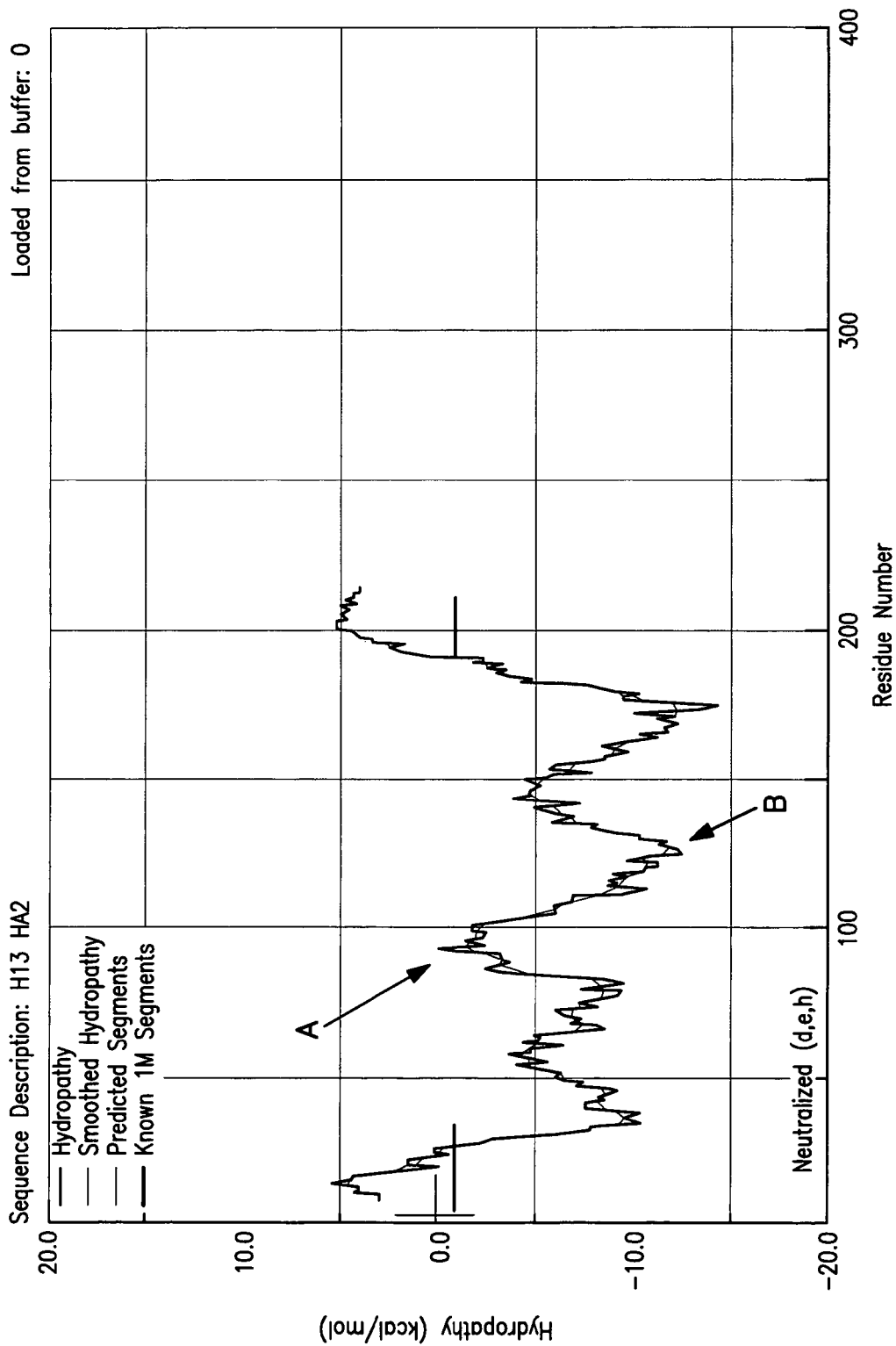
FIG. 17 shows a Wimley-White interfacial hydropathy plot for Influenza A H13 hemagglutinin 2.
Figure 18:
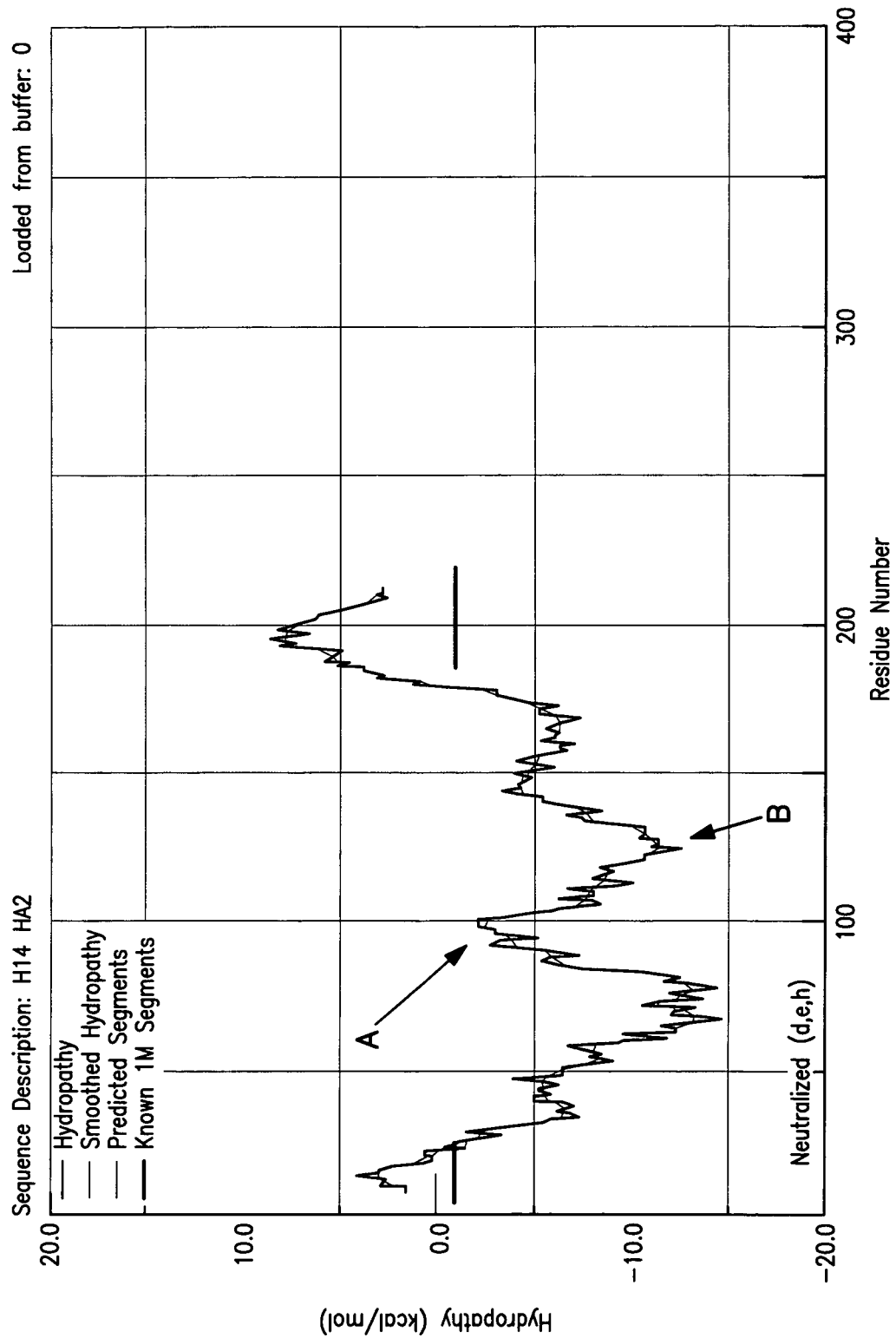
FIG. 18 shows a Wimley-White interfacial hydropathy plot for Influenza A H14 hemagglutinin 2.
Figure 19:
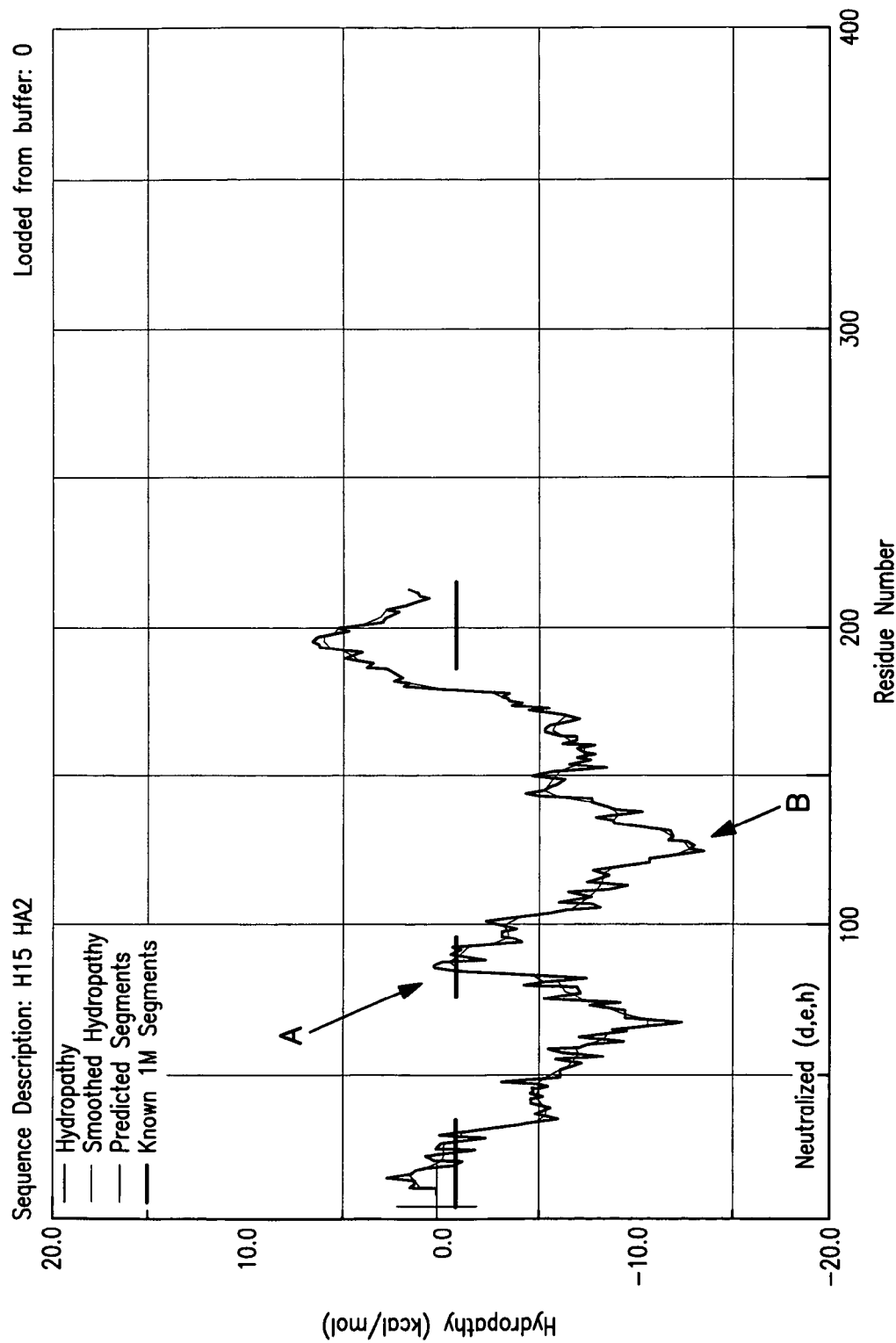
FIG. 19 shows a Wimley-White interfacial hydropathy plot for Influenza A H15 hemagglutinin 2.
Figure 20:
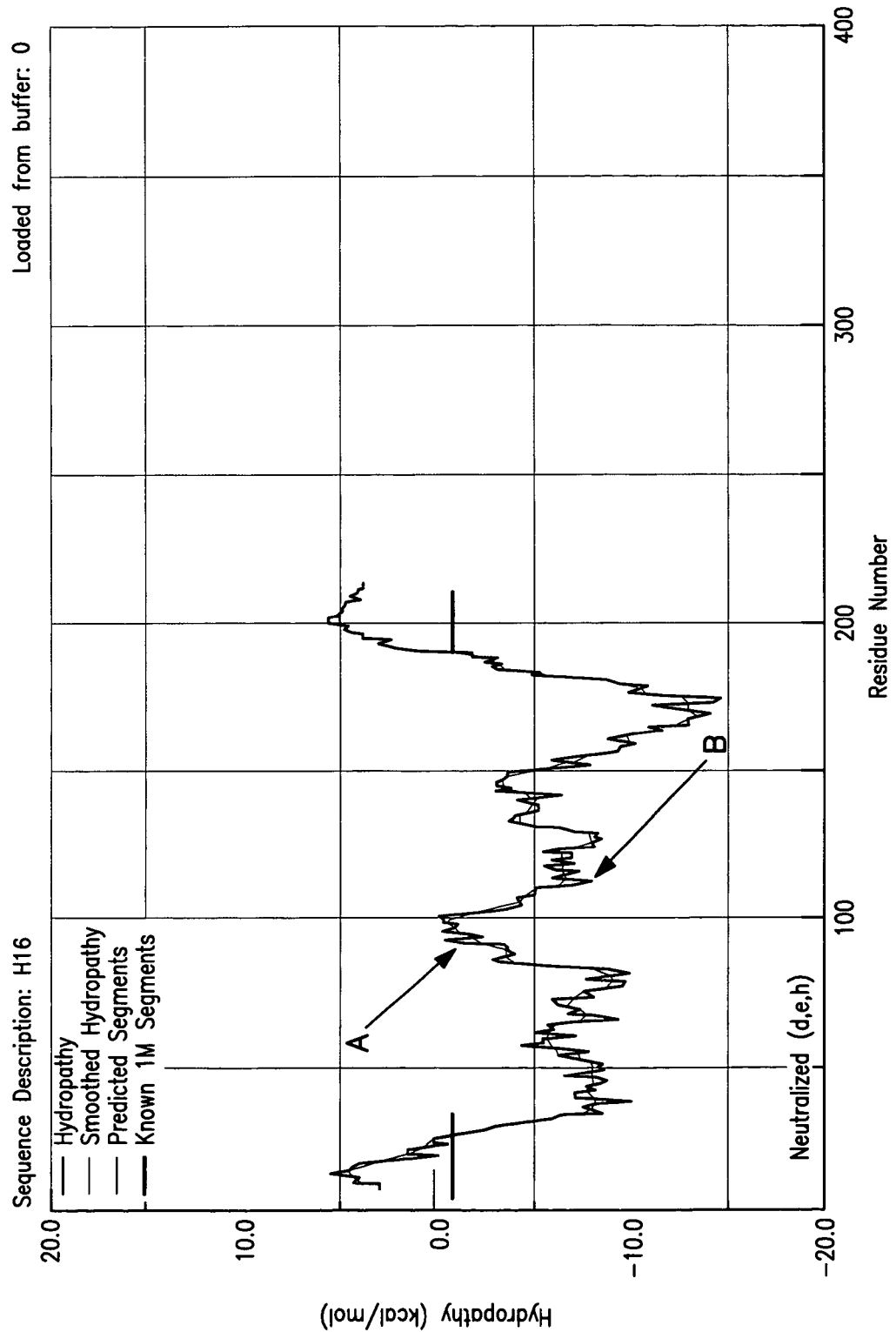
FIG. 20 shows a Wimley-White interfacial hydropathy plot for Influenza A H16 hemagglutinin 2.

Quantitative RT-PCR analysis and conserved primers to the influenza virus nucleoprotein gene provides reliable analyses of viral genomic RNA levels in tissue homogenates from treated and infected ferrets. Nasal aspirate samples were collected from the animals during the study period. The virus titers from those samples are shown in FIG. 7, Panel A. The results of analyses of ferret tissue homogenates taken from the brain, trachea liver, spleen and blood on Day 1 of the study are shown in Panel B of FIG. 7. The data in Panel A demonstrate that peak titers of influenza virus in ferret nasal washes were reduced by greater than 2.0 $\log_{10}$ and in the lungs by greater than 6.0 $\log_{10}$. These results indicate that F3 significantly reduced the replication of influenza virus in the upper respiratory tract of ferrets. The data in Panel B indicate the F3 effectively blocked spread of the virus to the lower respiratory tract and to other organs, as well.

Identification of the Influenza FIR.

The carboxy-terminus of the FIR of an influenza virus can be defined as the residue immediately preceding the first peptide sequence that exhibits a positively increasing interfacial hydrophobicity in a Wimley-White interfacial hydropathy plot that is found beyond the carboxy-terminus of the N-helix (residue 104). Table 3 below shows the Wimley-White interfacial hydrophobicity scale for proteins at membrane interfaces as described by Wimley and White in 1996. This hydrophobicity or hydropathy scale is based on the free energy change required to transfer a peptide residue from a hydrophobic membrane bilayer interface to an aqueous phase. In this scale, a positive free energy ($\Delta G$), in kilocalories per mole, indicates a more hydrophobic residue (i.e., energy must be added to transfer a hydrophobic residue from a hydrophobic membrane into water. Similarly, a negative free energy indicates a more hydrophilic residue.

In a plot of Wimley-White interfacial hydrophobicity, the FIR is characterized as a peak region of hydropathy (i.e., a region of relatively higher hydrophobicity including a local maximum in hydrophobicity situated between two local minima in hydrophobicity. This peak region begins in the N-helix of the HA2 protein and ends within about 15 residues beyond N-helix.

TABLE 3

Wimley-White Interfacial Hydrophobicity Scale

| X-residue | pH | $\Delta G$ (kcal mol$^{-1}$) |
|---|---|---|
| Ala | 8 | −0.17 ± 0.06 |
| Arg | 2 | −0.81 ± 0.11 |
| Asn | 8 | −0.42 ± 0.06 |
| Asp | 8 | −1.23 ± 0.07 |
| Asp | 2 | 0.07 ± 0.11 |
| Cys | 8 | 0.24 ± 0.06 |
| Gln | 8 | −0.58 ± 0.08 |
| Glu | 8 | −2.02 ± 0.11 |
| Glu | 2 | 0.01 ± 0.15 |
| Gly | 8 | −0.01 ± 0.05 |
| His | 8 | −0.17 ± 0.06 |
| His | 2 | −0.96 ± 0.12 |
| Ile | 8 | 0.31 ± 0.06 |
| Leu | 8 | 0.56 ± 0.04 |
| Lys | 2 | −0.99 ± 0.11 |
| Met | 8 | 0.23 ± 0.06 |
| Phe | 8 | 1.13 ± 0.05 |

TABLE 3-continued

Wimley-White Interfacial Hydrophobicity Scale

| X-residue | pH | $\Delta G$ (kcal mol$^{-1}$) |
|---|---|---|
| Pro | 8 | −0.45 ± 0.12 |
| Ser | 8 | −0.13 ± 0.08 |
| Thr | 8 | −0.14 ± 0.06 |
| Trp | 8 | 1.85 ± 0.06 |
| Tyr | 8 | 0.94 ± 0.06 |
| Val | 8 | −0.07 ± 0.05 |

Computer programs, such as the Membrane Protein Explorer (MPEx) available from the website: blanco.biomol.uci.edu/mpex, can be used to calculate an interfacial hydropathy profile for a protein or polypeptide. The MPEx program incorporates Wimley-White hydropathy scales and constitutes a preferred method of ascertaining the degree of interfacial hydrophobicity of these peptide sequences. The MPEx computer program was used to aid in characterizing the carboxy-terminus of the FIR in each of the thirteen sequenced HA2 variants shown in FIG. 2. The MPEx computer program plots the Wimley-White interfacial hydropathy score for the protein or peptide of interest by averaging the whole-residue hydropathy values for all residues in a window consisting of a fixed number of consecutive amino acid residues (preferably about 19 residues), and plotting the average value of the hydropathy in that window as the hydropathy score for the middle residue in the window. The window is then shifted by one residue moving from the amino-terminal to carboxy-terminal direction, and the process is repeated until the hydropathy score for each residue in the region of interest has been determined.

Wimley-White interfacial hydropathy profiles for all of the 13 HA2 subtypes shown in FIG. 2 were prepared using the MPEx program, using a window of 19 amino acid residues. The amino-terminus of the FIR is found at the point within the N-helix of the protein in which interfacial hydropathy begins to steadily increase after a local minimum (i.e., at residue 77 for all of the HA2 proteins examined to date). The carboxy-terminus of the FIR is the residue immediately preceding the first local minimum in hydrophobicity beyond the N-helix, i.e., the residue immediately before the first peptide sequence with positively increasing interfacial hydrophobicity that is found beyond the carboxy-terminus of the N-helix. In each influenza A HA2 subtype shown in FIG. 2, the N-helix ends at residue 104. The plot of the Wimley-White hydropathy scores does not need to cross above the zero axis in order to be useful in ascertaining the location of the carboxy-terminus of a FIR, there merely has to be an increase in hydropathy score relative to the preceding peptide residues.

FIGS. 8-20 show the MPEx Wimley-White hydropathy profiles of the thirteen sequenced variants of the HA2 fusion protein of influenza A (in these Figures, "A" indicates the FIR of the peptide, characterized by a peak in the hydropathy plot). The carboxy-terminus of the FIR is indicated in each of FIGS. 8-20 by a "B". From the analyses, it has been determined that the amino-terminus of the FIR begins at residue 77 of the HA2 sequence, in each viral HA2 subtype. The carboxy-terminus of the FIR varies between residue 110 and 119 for each of the HA2 subtypes. The FIR region is highlighted in FIG. 2 within a darkened border around residues 77 to 110 or 119.

Peptides of the invention having improved activity can be identified by preparing nested sets of peptides, which are either longer (corresponding to flanking sequences of HA) or are truncated compared to an active target inhibitor protein portion of an FIR (e.g., SEQ ID NO: 2). Peptides that extend the target HA amino acid sequence by 3-6 amino acids at the amino- or carboxy-termini of the peptides are tested systematically against a battery of influenza viruses to determine whether the amino acid segments on either side of the sequence contributes to an increased inhibition of infectivity. If a peptide that is longer than the target sequence inhibits infectivity of influenza A virus with a lower $IC_{50}$ than the target, then peptides having fewer additional amino acids than the target can be systematically tested to determine the minimum peptide with infectivity inhibiting activity. Active peptides specific for a particular type/or subtype can also be tested against several additional strains of the same type or subtype of influenza virus to determine the breadth of the inhibitory activity. For example, a target peptide based on SEQ ID NO: 5 should inhibit multiple H5 subtype viruses with $IC_{50}$<100 nM.

Other peptide variants suitable for testing can be determined by systematically altering residues in the target sequence to alanine residues (referred to herein as "alanine scanning"). Comparison of the alanine-modified peptides with wild-type peptides identifies residues important for fusion/infectivity inhibition. If more than one amino acid affects inhibition, additional peptides can be synthesized with alterations at each residue of significance.

The functional domains putatively targeted by peptides of the invention (e.g., SEQ ID NO: 3 through SEQ ID NO: 13) are alpha-helical in configuration. Peptide variations that improve or disrupt helicity may alter the activity of the peptides as influenza A virus fusion/infectivity inhibitors. Accordingly, variants or analogs of active peptides can be prepared by substituting amino acids that favor helical content, such as aminobutyrate (AIB) or glutamic acid for other amino acids. Likewise, the addition of prolines or glycines to a peptide can disrupt alpha-helical content, which informatively will either improve or reduce inhibitory activity. Additional analog peptides with increased binding to HA2 identified by screening combinatorial libraries can also be tested for inhibition of influenza virus infectivity.

Peptidases in the nasal cavity or the lung could potentially limit the utility of platform therapeutics in vivo. If a peptide variant that is active in plaque reduction assays is being degraded or rapidly cleared from respiratory tissues, additional modifications to increase peptide stability and retention can be performed. Dry powder or alterations/additions to the formulation can improve the stability of peptides. Cyclized peptide analogs, with two more cysteines added to provide a disulfide cyclized peptide, can stabilize secondary structures and make the peptide more resistant to degradation. Substitution of two or more residues with proline also can greatly increase the stability of synthetic peptides. Various amino- or carboxy-terminal modifications or conjugation to proteins (e.g., serum albumin) or lipids (e.g., myristic acid) can also improve stability of activity of viral inhibitory peptides (Qureshi et al., 1990), as can the introduction of non-natural amino acids (hydroxyproline or D-amino acids) at peptidase cleavage sites.

In the event that inhibitory peptides demonstrate low solubility in aqueous solutions, peptide variants can be synthesized with a variation of sequence ASKSKSK (SEQ ID NO: 15) added to the carboxy-terminus to increase solubility of the peptide. This sequence has been shown to increase the solubility of the model peptides, while preserving secondary structure. Increased solubility may also lower the concentration required to inhibit influenza virus envelope-mediated fusion.

Conserved Residue Sequences.

It has been observed that a highly conserved sequence, YNAELL (SEQ ID NO: 1), lies within the FIRs of eleven of the thirteen sequenced HA2 subtypes and that the corresponding sequence YNAKLL (SEQ ID NO: 16), which exhibits a single amino acid substitution in SEQ ID NO: 1, appears in the other two subtypes. Only one other sequence within the thirteen sequenced HA2 variants is more highly conserved than YNAELL (SEQ ID NO: 1). That sequence, AIAGFIE (SEQ ID NO: 31, residues 5-11 of the full length protein), lies within the fusion peptide, or FP, of the HA2 protein. The FP domain is one of the five previously known domains of Class I viral fusion proteins, and the FP domain was previously known to play an important role in the virus to cell fusion process.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

The following references are each incorporated by reference in their entirety:

Chang, D. K., and Hsu, C. S. (2007). Biophysical evidence of two docking sites for the carboxyl heptad repeat region within the amino heptad repeat region of gp41 of immunodeficiency virus type 1. *Antiviral. Res.* 74, 51-8.

Cianci, C., Yu, K. L., Dischino, D. D., Harte, W., Deshpande, M. Luo, G., Colonno, R. J., Meanwell, N. A., and Krystal, M. (1999). PH-dependent changes in photoaffinity labeling patterns of the H1 influenza virus hemagglutinin by using an inhibitor of viral fusion. *J. Virol.* 73, 1785-94.

Debnath, A. K. (2006). Prospects and strategies for the discovery and development of small-molecule inhibitors of six-helix bundle formation in class 1 viral fusion proteins. *Curr. Opin. Investig. Drugs* 7, 118-27.

Este, J. A., and Telenti, A. (2007). HIV entry inhibitors. *Lancet* 370, 81-8.

Govorkova, E. A., Rehg, J. E., Krauss, S., Yen, H. L., Guan, Y., Peiris, M., Nguyen, T. D., Hanh, T. H., Puthavathana, P., Long, H. T., Buranathai, C., Lim, W., Webster, R. G., and Hoffman, E. (2005). Lethality to ferrets of H5N1 influenza viruses isolated from humans and poultry in 2004. *J. Virol.* 79, 2191-8.

Hampson, A. W. (2006). Ferrets and the challenges of H5N1 vaccine formulation. *J. Infect. Dis.* 194, 143-5.

Hoffman, L. R., Kuntz, I. D., and White, J. M. (1997). Structure-based identification of an inducer of the low-pH conformational change in the influenza virus hemagglutinin: irreversible inhibition of infectivity. *J. Virol.* 71, 8808-20.

Lu, X., Tumpey, T. M., Morken, T., Zaki, S. R., Cox, N. J., and Katz, J. M. (1999). A mouse model for the evaluation of pathogenesis and immunity to influenza A (H5N1) viruses isolated from humans. *J. Virol.* 73, 5903-11.

Luo, G., Colonno, R., and Krystal, M. (1996). Characterization of a hemagglutinin-specific inhibitor of influenza A virus. *Virology* 226, 66-76.

Luo G., Torri, A., Hare, W. E., Danetz, S., Cianci, C., Tiley, L., Day, S. Mullaney, D., Yu, K. L., Ouellet, C., Dextraze, P., Meanwell, N., Colonno, R. And Krystal, M. (1997). Molecular mechanism underlying the action of a novel fusion inhibitor of influenza A virus. *J. Virol.* 71, 4062-70.

Maher, J. A. and DeStefano, J. (2004). The ferret: an animal model to study influenza virus. *Lab. Anim.* (NY) 33, 50-3.

Matrosovich, M., Matrosovich, T., Garten, W., and Klenk, H. (2006). New low-viscosity overlay medium for viral plaque assays. *J. Virol.* 3, 63.

Platt, E. J., Durnin, J. P., and Kabat, D. (2005). Kinetic factors control efficiencies of cell entry, efficacies of entry inhibitors, and mechanisms of adaptation of human immunodeficiency virus. *J. Virol.* 79, 4347-56.

Qureshi, N., Coy, D., Garry, R., and La, H. (1990). Characterization of a putative cellular receptor for HIV-1 transmembrane glycoprotein using synthetic peptides. *AIDS* 4, 553-558.

Thiry, E., Zicola, A., Addie, D., Egberink, H., Hartmann, K., Lutz, H., Poulet, H., and Horzinek, M. C. (2007). Highly pathogenic avian influenza H5N1 virus in cats and other carnivores. *Vet. Microbiol.* 122, 25-31.

Vahlenkamp, t. W., and Harder, T. C. (2006). Influenza virus infections in mammals. *Berl. Munch. Tierarztl. Wochenschr.* 119, 123-31.

van Riel, D., Munster, V. J., de Wit, E., Rimmelzwaan, G. F., Fouchier, R. A., Osterhaus, A. D., and Kuiken, T. (2006). H5N1 virus attachment to lower respiratory tract. *Science* 312, 399.

van Riel, D., Munster, V. J., de Wit, E., Rimmelzwaan, G. F., Fouchier, R. A., Osterhaus, A. D., and Kuiken, T. (2007) Human and avian influenza viruses target different cells in the lower respiratory tract of humans and other mammals. *Am. J. Pathol.* 171, 1215-23.

Wimley, W. C., White, S. H. (1996). Experimentally determined hydrophobicity scale for proteins at membrane interfaces. *Nature Struct. Biol.* 3(10), 842-848.

Yen, H. L., Lipatov, A. S., Ilyushina, N. A., Govorkova, E. A., Franks, J., Yilmaz, N., Douglas, A., Hay, A., Krauss, S., Rehg, J. E., Hoffman, E., and Webster, R. G. (2007). Inefficient transmission of H5N1 influenza viruses in a ferret contact model. *J. Virol.* 81, 6890-8.

Zhu, J., Jiang, X., Lui, Y., Tien, P., and Gao, G. F. (2005). Design and characterization of viral polypeptide inhibitors targeting Newcastle disease virus fusion. *J. Mol. Biol.* 354, 601-13.

---

We claim:

1. A pharmaceutical composition for the treatment of an influenza virus infection by inhibiting fusion of the virus with a host cell membrane, the composition comprising:

a pharmaceutically acceptable carrier; and an isolated polypeptide consisting of an amino acid sequence selected from the group consisting of SEQ ID NO: 3, SEQ ID NO: 4, and a variant of SEQ ID NO: 3 or 4 including one or more amino acid substitutions in said amino acid sequence, the variant comprising the sequence YNAELL (SEQ ID NO: 1) and sharing at least 50 percent sequence identity with SEQ ID NO: 3.

2. A method of interfering with fusion of an influenza virus envelope with a host cell membrane comprising contacting an influenza virus with the composition of claim 1.

3. The pharmaceutical composition of claim 1 wherein the pharmaceutically acceptable carrier comprises a buffered saline solution.

4. The pharmaceutical composition of claim 1 wherein the composition is in the form of an inhalable powder.

5. The pharmaceutical composition of claim 1 wherein the amino acid sequence of the polypeptide consists of SEQ ID NO: 3.

6. The pharmaceutical composition of claim 1 wherein the amino acid sequence of the polypeptide consists of SEQ ID NO: 4.

7. The pharmaceutical composition of claim 1 wherein the amino acid sequence of the polypeptide consists of a variant of SEQ ID NO: 3 comprising one or more amino acid substitutions selected from the group consisting of V1I, V1L, V1A, V1G, V1T, V1S, V1M, E2D, E2K, E2R, D3E, T4G, T4S, T4Q, T4N, K5F, K5M, K5I, K5V, K5L, K5A, I6L, I6V, I6A, I6T, I6S, I6Q, I6N, D7E, L8I, L8V, L8A, W9Y, S10T, S10G, S10A, and S10M.

8. The pharmaceutical composition of claim 1 wherein the amino acid sequence of the polypeptide consists of a variant of SEQ ID NO: 4 comprising one or more amino acid substitutions selected from the group consisting of V1I, V1L, V1A, V1G, V1T, V1S, V1M, D2E, D2K, D2R, D3E, G4T, G4S, G4Q, G4N, F5K, F5M, F5I, F5V, F5L, F5A, L6I, L6V, L6A, L6T, L6S, L6Q, L6N, D7E, I8L, I8V, I8A, W9Y, T10S, T10G, T10A, and T10M.

9. The pharmaceutical composition of claim 1 wherein the polypeptide includes a lipid substituent bound to an amino acid residue of the polypeptide.

10. A pharmaceutical composition for the treatment of an influenza virus infection by inhibiting fusion of the virus with a host cell membrane, the composition comprising:
   a buffered saline solution; and
   an isolated polypeptide consisting of an amino acid sequence selected from the group consisting of SEQ ID NO: 3 and a variant of SEQ ID NO: 3 including one or more amino acid substitutions in said amino acid sequence selected from the group consisting of V1I, V1L, V1A, V1G, V1T, V1S, V1M, E2D, E2K, E2R, D3E, T4G, T4S, T4Q, T4N, K5F, K5M, K5I, K5V, K5L, K5A, I6L, I6V, I6A, I6T, I6S, I6Q, I6N, D7E, L8I, L8V, L8A, W9Y, S10T, S10G, S10A, and S10M, the variant comprising the sequence YNAELL (SEQ ID NO: 1) and sharing at least 50 percent sequence identity with SEQ ID NO: 3.

11. The pharmaceutical composition of claim 10 wherein the polypeptide includes a lipid substituent bound to an amino acid residue of the polypeptide.

12. A method of interfering with fusion of an influenza virus envelope with a host cell membrane comprising contacting an influenza virus with the composition of claim 3.

13. A method of interfering with fusion of an influenza virus envelope with a host cell membrane comprising contacting an influenza virus with the composition of claim 4.

14. A method of interfering with fusion of an influenza virus envelope with a host cell membrane comprising contacting an influenza virus with the composition of claim 5.

15. A method of interfering with fusion of an influenza virus envelope with a host cell membrane comprising contacting an influenza virus with the composition of claim 6.

16. A method of interfering with fusion of an influenza virus envelope with a host cell membrane comprising contacting an influenza virus with the composition of claim 7.

17. A method of interfering with fusion of an influenza virus envelope with a host cell membrane comprising contacting an influenza virus with the composition of claim 8.

18. A method of interfering with fusion of an influenza virus envelope with a host cell membrane comprising contacting an influenza virus with the composition of claim 9.

19. A method of interfering with fusion of an influenza virus envelope with a host cell membrane comprising contacting an influenza virus with the composition of claim 10.

20. A method of interfering with fusion of an influenza virus envelope with a host cell membrane comprising contacting an influenza virus with the composition of claim 11.

* * * * *

UNITED STATES PATENT AND TRADEMARK OFFICE
CERTIFICATE OF CORRECTION

PATENT NO. : 8,222,204 B2
APPLICATION NO. : 12/378561
DATED : July 17, 2012
INVENTOR(S) : Robert F. Garry et al.

It is certified that error appears in the above-identified patent and that said Letters Patent is hereby corrected as shown below:

Column 1, line 64, delete the word "heptade" and insert --heptad--.

Column 3, line 43, delete the term "N33Q".
line 43, delete "Q34E", first occurrence.

Column 4, line 4, delete "mM" and insert --nM--.

Column 8, Table 1, line 34, delete "I16A" and insert --T16A--.
Table 1, line 57, after "A30M" delete "." and insert --,--.
Table 1, line 66, delete "I27M" and insert --I37M--.

Column 12, line 56, delete "thr" and insert --the--.

Column 13, line 44, delete the word "stains" and insert --strains--.
line 45, delete the word "of", first occurrence.
line 58, delete "mM" and insert --nM--.

Column 14, line 14, "Calcdonia" and insert --Caledonia--.

Column 15, line 40, delete "begins" and insert --begin--.
line 56, delete "A/PR/8134" and insert --A/PR/8/34--.
line 59, delete "Calcdonia" and insert --Caledonia--.

Column 16, line 31, delete "2/5in" and insert --2/5 in--.
line 32, delete "1/6in" and insert --1/6 in--.
line 55, after the word "the" delete the word "in".

Signed and Sealed this
Eighteenth Day of December, 2012

David J. Kappos
*Director of the United States Patent and Trademark Office*

CERTIFICATE OF CORRECTION (continued)
U.S. Pat. No. 8,222,204 B2

Column 17, line 13, after the word "trachea" insert --,--.
          line 35, delete "(AG)" and insert --($\Delta$G)--.
          line 38, after the word "water" insert --)--.
          line 44, after the word "hydrophobicity" insert --)--.

In the References:

Column 20, line 65, delete "PH" and insert --pH--.

Column 22, line 13, delete "t." and insert --T.--.

In the Claims:

Column 47, line 17, claim 8, delete "FSK" and insert --F5K--.
          line 17, claim 8, delete "FSM" and insert --F5M--.
          line 35, claim 10, delete "S 10G" and insert --S10G--.

SEQUENCE LISTING

```
<160> NUMBER OF SEQ ID NOS: 31

<210> SEQ ID NO 1
<211> LENGTH: 6
<212> TYPE: PRT
<213> ORGANISM: Influenza A virus
<220> FEATURE:
<223> OTHER INFORMATION: Residues 94-99 of influenza A/H3
      hemagglutinin 2

<400> SEQUENCE: 1

Tyr Asn Ala Glu Leu Leu
1               5

<210> SEQ ID NO 2
<211> LENGTH: 42
<212> TYPE: PRT
<213> ORGANISM: Influenza A virus
<220> FEATURE:
<223> OTHER INFORMATION: Residues 72-116 of influenza A/H3
      hemagglutinin 2

<400> SEQUENCE: 2

Glu Val Glu Gly Arg Ile Gln Asp Leu Glu Lys Tyr Val Glu Asp Thr
1               5                   10                  15

Lys Ile Asp Leu Trp Ser Tyr Asn Ala Glu Leu Leu Val Ala Leu Glu
            20                  25                  30
```

Asn Gln His Thr Ile Asp Leu Thr Asp Ser
          35                  40

<210> SEQ ID NO 3
<211> LENGTH: 16
<212> TYPE: PRT
<213> ORGANISM: Influenza A virus
<220> FEATURE:
<223> OTHER INFORMATION: Residues 84-99 of influenza A/H3, A/H4,
      and A/H14 hemagglutinin 2

<400> SEQUENCE: 3

Val Glu Asp Thr Lys Ile Asp Leu Trp Ser Tyr Asn Ala Glu Leu Leu
1               5                   10                  15

<210> SEQ ID NO 4
<211> LENGTH: 19
<212> TYPE: PRT
<213> ORGANISM: Influenza A virus
<220> FEATURE:
<223> OTHER INFORMATION: Residues 84-102 of influenza A/H1
      hemagglutinin 2

<400> SEQUENCE: 4

Val Asp Asp Gly Phe Leu Asp Ile Trp Thr Tyr Asn Ala Glu Leu Leu
1               5                   10                  15

Val Leu Leu

<210> SEQ ID NO 5
<211> LENGTH: 16
<212> TYPE: PRT
<213> ORGANISM: Influenza A virus
<220> FEATURE:
<223> OTHER INFORMATION: Residues 84-99 of influenza A/H5
      hemagglutinin 2

<400> SEQUENCE: 5

Met Glu Asp Gly Phe Leu Asp Val Trp Thr Tyr Asn Ala Glu Leu Leu
1               5                   10                  15

<210> SEQ ID NO 6
<211> LENGTH: 16
<212> TYPE: PRT
<213> ORGANISM: Influenza A virus
<220> FEATURE:
<223> OTHER INFORMATION: Residues 84-99 of influenza A/H7
      hemagglutinin 2

<400> SEQUENCE: 6

Thr Arg Asp Ala Met Thr Glu Val Trp Ser Tyr Asn Ala Glu Leu Leu
1               5                   10                  15

<210> SEQ ID NO 7
<211> LENGTH: 16
<212> TYPE: PRT
<213> ORGANISM: Influenza A virus
<220> FEATURE:
<223> OTHER INFORMATION: Residues 84-99 of influenza A/H9
      hemagglutinin 2

<400> SEQUENCE: 7

Val Asp Asp Gln Ile Gln Asp Ile Trp Ala Tyr Asn Ala Glu Leu Leu
1               5                   10                  15

<210> SEQ ID NO 8
<211> LENGTH: 16
<212> TYPE: PRT
<213> ORGANISM: Influenza B virus

```
<220> FEATURE:
<223> OTHER INFORMATION: Residues 84-99 of influenza B
      hemagglutinin 2

<400> SEQUENCE: 8

Val Asp Asp Leu Arg Ala Asp Thr Ile Ser Ser Gln Ile Glu Leu Ala
1               5                   10                  15

<210> SEQ ID NO 9
<211> LENGTH: 16
<212> TYPE: PRT
<213> ORGANISM: Influenza A virus
<220> FEATURE:
<223> OTHER INFORMATION: Residues 84-99 of influenza A/H2 and A/H6
      hemagglutinin 2

<400> SEQUENCE: 9

Met Glu Asp Gly Phe Leu Asp Val Trp Thr Tyr Asn Ala Glu Leu Leu
1               5                   10                  15

<210> SEQ ID NO 10
<211> LENGTH: 16
<212> TYPE: PRT
<213> ORGANISM: Influenza A virus
<220> FEATURE:
<223> OTHER INFORMATION: Residues 84-99 of influenza A/H10
      hemagglutinin 2

<400> SEQUENCE: 10

Thr Lys Asp Ser Ile Thr Asp Ile Trp Thr Tyr Asn Ala Glu Leu Leu
1               5                   10                  15

<210> SEQ ID NO 11
<211> LENGTH: 16
<212> TYPE: PRT
<213> ORGANISM: Influenza A virus
<220> FEATURE:
<223> OTHER INFORMATION: Residues 84-99 of influenza A/H13
      hemagglutinin 2

<400> SEQUENCE: 11

Ile Asp Asp Ala Val Thr Asp Ile Trp Ser Tyr Asn Ala Lys Leu Leu
1               5                   10                  15

<210> SEQ ID NO 12
<211> LENGTH: 16
<212> TYPE: PRT
<213> ORGANISM: Influenza A virus
<220> FEATURE:
<223> OTHER INFORMATION: Residues 84-99 of influenza A/H15
      hemagglutinin 2

<400> SEQUENCE: 12

Thr Arg Asp Ser Leu Thr Glu Ile Trp Ser Tyr Asn Ala Glu Leu Leu
1               5                   10                  15

<210> SEQ ID NO 13
<211> LENGTH: 16
<212> TYPE: PRT
<213> ORGANISM: Influenza A virus
<220> FEATURE:
<223> OTHER INFORMATION: Residues 84-99 of influenza A/H16
      hemagglutinin 2

<400> SEQUENCE: 13

Val Asp Asp Ala Val Thr Asp Ile Trp Ser Tyr Asn Ala Lys Leu Leu
1               5                   10                  15
```

```
<210> SEQ ID NO 14
<211> LENGTH: 16
<212> TYPE: PRT
<213> ORGANISM: Artificial Sequence
<220> FEATURE:
<223> OTHER INFORMATION: Scrambled version of residues 84-99 of
      influenza A/H3 HA2
<223> OTHER INFORMATION: Synthetic peptide

<400> SEQUENCE: 14

Ser Trp Leu Val Asn Lys Ile Tyr Leu Thr Asp Asp Glu Val Glu Leu
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Thr Arg Asp Ser Leu Thr Glu Ile Trp Ser Tyr Asn Ala Glu Leu Leu
 1               5                  10                  15

<210> SEQ ID NO 16
<211> LENGTH: 6
<212> TYPE: PRT
<213> ORGANISM: Influenza A virus
<220> FEATURE:
<223> OTHER INFORMATION: Residues 94-99 of influenza A/H13 and A/H16
      hemagglutinin 2

<400> SEQUENCE: 16

Tyr Asn Ala Lys Leu Leu
 1               5

<210> SEQ ID NO 17
<211> LENGTH: 222
<212> TYPE: PRT
<213> ORGANISM: Influenza A virus
<220> FEATURE:
<223> OTHER INFORMATION: Influenza A/H1 hemagglutinin 2

<400> SEQUENCE: 17

Gly Leu Phe Gly Ala Ile Ala Gly Phe Ile Glu Gly Gly Trp Thr Gly
 1               5                  10                  15

Met Ile Asp Gly Trp Tyr Gly Tyr His His Gln Asn Glu Gln Gly Ser
                20                  25                  30

Gly Tyr Ala Ala Asp Gln Lys Ser Thr Gln Asn Ala Ile Asn Gly Ile
            35                  40                  45

Thr Asn Lys Val Asn Ser Val Ile Glu Lys Met Asn Thr Gln Phe Thr
 50                  55                  60

Ala Val Gly Lys Glu Phe Asn Asn Leu Glu Lys Arg Met Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Leu Asn Val Lys Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160
```

```
Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
                180                 185                 190

Val Ala Ser Ser Leu Val Leu Val Ser Leu Gly Ala Ile Ser Phe
                195                 200                 205

Trp Met Cys Ser Asn Gly Ser Leu Gln Cys Arg Ile Cys Ile
                210                 215                 220
```

<210> SEQ ID NO 18
<211> LENGTH: 222
<212> TYPE: PRT
<213> ORGANISM: Influenza A virus
<220> FEATURE:
<223> OTHER INFORMATION: Influenza A/H2 hemagglutinin 2

<400> SEQUENCE: 18

```
Gly Leu Phe Gly Ala Ile Ala Gly Phe Ile Glu Gly Gly Trp Gln Gly
  1               5                  10                  15

Met Val Asp Gly Trp Tyr Gly Tyr His His Ser Asn Asp Gln Gly Ser
                 20                  25                  30

Gly Tyr Ala Ala Asp Lys Glu Ser Thr Gln Lys Ala Phe Asp Gly Ile
                 35                  40                  45

Thr Asn Lys Val Asn Ser Val Ile Glu Lys Met Asn Thr Gln Phe Glu
             50                  55                  60

Ala Val Gly Lys Glu Phe Ser Asn Leu Glu Arg Arg Leu Glu Asn Leu
 65                  70                  75                  80

Asn Lys Lys Met Glu Asp Gly Phe Leu Asp Val Trp Thr Tyr Asn Ala
                 85                  90                  95

Glu Leu Leu Val Leu Met Glu Asn Glu Arg Thr Leu Asp Phe His Asp
                100                 105                 110

Ser Asn Val Lys Asn Leu Tyr Asp Lys Val Arg Met Gln Leu Arg Asp
                115                 120                 125

Asn Val Lys Glu Leu Gly Asn Gly Cys Phe Glu Phe Tyr His Lys Cys
            130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Ser Met Gly Val Tyr Gln Ile Leu Ala Ile Tyr Ala Thr
                180                 185                 190

Val Ala Gly Ser Leu Ser Leu Ala Ile Met Met Ala Gly Ile Ser Phe
                195                 200                 205

Trp Met Cys Ser Asn Gly Ser Leu Gln Cys Arg Ile Cys Ile
                210                 215                 220
```

<210> SEQ ID NO 19
<211> LENGTH: 221
<212> TYPE: PRT
<213> ORGANISM: Influenza A virus
<220> FEATURE:
<223> OTHER INFORMATION: Influenza A/H3 hemagglutinin 2

<400> SEQUENCE: 19

```
Gly Leu Phe Ser Ala Ile Ala Gly Phe Ile Glu Asn Gly Trp Glu Gly
  1               5                  10                  15

Met Ile Asp Gly Trp Tyr Gly Phe Arg His Gln Asn Ser Glu Gly Thr
                 20                  25                  30
```

```
Gly Gln Ala Ala Asp Leu Lys Ser Thr Gln Ala Ala Ile Asp Gln Ile
            35                  40                  45

Asn Gly Lys Leu Asn Arg Val Ile Glu Lys Thr Asn Glu Lys Phe His
 50                  55                  60

Gln Ile Glu Lys Glu Phe Ser Glu Val Glu Gly Arg Ile Gln Asp Leu
 65                  70                  75                  80

Glu Lys Tyr Val Glu Asp Thr Lys Ile Asp Leu Trp Ser Tyr Asn Ala
                 85                  90                  95

Glu Leu Leu Val Ala Leu Glu Asn Gln His Thr Ile Asp Leu Thr Asp
                100                 105                 110

Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
        130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
        210                 215                 220

<210> SEQ ID NO 20
<211> LENGTH: 221
<212> TYPE: PRT
<213> ORGANISM: Influenza A virus
<220> FEATURE:
<223> OTHER INFORMATION: Influenza A/H4 hemagglutinin 2

<400> SEQUENCE: 20

Gly Leu Phe Gly Ala Ile Ala Gly Phe Ile Glu Asn Gly Trp Gln Gly
  1               5                  10                  15

Leu Ile Asp Gly Trp Tyr Gly Phe Arg His Gln Asn Ala Glu Gly Thr
             20                  25                  30

Gly Thr Ala Ala Asp Leu Lys Ser Thr Gln Ala Ala Ile Asp Gln Thr
            35                  40                  45

Asn Gly Lys Leu Asn Arg Leu Ile Glu Lys Thr Asn Glu Lys Tyr His
 50                  55                  60

Gln Ile Glu Lys Glu Phe Glu Gln Val Glu Gly Arg Ile Gln Asp Leu
 65                  70                  75                  80

Glu Lys Tyr Val Glu Asp Thr Lys Ile Asp Leu Trp Ser Tyr Asn Ala
                 85                  90                  95

Glu Leu Leu Val Ala Leu Glu Asn Gln His Thr Ile Asp Val Thr Asp
                100                 105                 110

Ser Glu Met Asn Lys Leu Phe Glu Arg Val Arg Arg Gln Leu Arg Glu
            115                 120                 125

Asn Ala Glu Asp Lys Gly Asn Gly Cys Phe Glu Ile Phe His Gln Cys
        130                 135                 140

Asp Asn Ser Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Asp
                165                 170                 175
```

```
Lys Leu Thr Gln Gly Tyr Lys Asp Ile Ile Leu Trp Ile Ser Phe Ser
            180                 185                 190

Ile Ser Cys Phe Leu Leu Val Ala Leu Leu Leu Ala Phe Ile Leu Trp
            195                 200                 205

Ala Cys Gln Asn Gly Asn Ile Arg Cys Gln Ile Cys Ile
            210                 215                 220

<210> SEQ ID NO 21
<211> LENGTH: 219
<212> TYPE: PRT
<213> ORGANISM: Influenza A virus
<220> FEATURE:
<223> OTHER INFORMATION: Influenza A/H5 hemagglutinin 2

<400> SEQUENCE: 21

Gly Leu Phe Gly Ala Ile Ala Gly Phe Ile Glu Gly Gly Trp Gln Gly
  1               5                  10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Val
        35                  40                  45

Thr Asn Lys Val Asn Ser Ile Ile Asp Lys Met Asn Thr Gln Phe Glu
 50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Leu Gln Leu Arg Asp
        115                 120                 125

Asn Ala Lys Glu Leu Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Asn Gly Val
                165                 170                 175

Lys Leu Glu Ser Ile Gly Ile Tyr Gln Ile Leu Ser Ile Tyr Ser Thr
            180                 185                 190

Val Ala Ser Ser Leu Ala Leu Ala Ile Met Val Ala Gly Leu Ser Leu
        195                 200                 205

Trp Met Cys Ser Asn Gly Ser Leu Gln Cys Arg
    210                 215

<210> SEQ ID NO 22
<211> LENGTH: 222
<212> TYPE: PRT
<213> ORGANISM: Influenza A virus
<220> FEATURE:
<223> OTHER INFORMATION: Influenza A/H6 hemagglutinin 2

<400> SEQUENCE: 22

Gly Leu Phe Gly Ala Ile Ala Gly Phe Ile Glu Gly Gly Trp Thr Gly
  1               5                  10                  15

Leu Val Asp Gly Trp Tyr Gly Tyr His His Glu Asn Ser Gln Gly Ser
            20                  25                  30

Gly Tyr Ala Ala Asp Arg Glu Ser Thr Gln Lys Ala Ile Asp Gly Ile
        35                  40                  45
```

```
Thr Asn Lys Val Asn Ser Ile Ile Asp Lys Met Asn Thr Gln Phe Glu
     50                  55                  60

Ala Val Asp His Glu Phe Ser Asn Leu Glu Arg Arg Ile Asp Asn Met
 65                  70                  75                  80

Asn Lys Arg Met Glu Asp Gly Phe Leu Asp Val Trp Thr Tyr Asn Ala
                 85                  90                  95

Glu Leu Leu Val Leu Leu Glu Asn Glu Arg Thr Leu Asp Leu His Asp
                100                 105                 110

Ala Asn Val Lys Ser Leu His Glu Lys Val Lys Ser Gln Leu Arg Asp
            115                 120                 125

Asn Ala Asn Asp Leu Gly Asn Gly Cys Phe Glu Phe Trp His Lys Cys
        130                 135                 140

Asp Asn Glu Cys Ile Glu Ser Val Lys Asn Gly Thr Tyr Asn Tyr Pro
145                 150                 155                 160

Lys Tyr His Asp Glu Ser Lys Leu Asn Arg Gln Lys Ile Glu Ser Val
                165                 170                 175

Lys Leu Glu Asn Leu Gly Val Tyr Gln Ile Leu Ala Ile Tyr Ser Thr
                180                 185                 190

Val Ser Ser Ser Leu Val Leu Val Gly Leu Ile Ile Ala Met Gly Leu
            195                 200                 205

Trp Met Cys Ser Asn Gly Ser Met Gln Cys Arg Ile Cys Ile
    210                 215                 220

<210> SEQ ID NO 23
<211> LENGTH: 221
<212> TYPE: PRT
<213> ORGANISM: Influenza A virus
<220> FEATURE:
<223> OTHER INFORMATION: Influenza A/H7 hemagglutinin 2

<400> SEQUENCE: 23

Gly Leu Phe Gly Ala Ile Ala Gly Phe Ile Glu Asn Gly Trp Glu Gly
  1               5                  10                  15

Leu Ile Asp Gly Trp Tyr Gly Phe Arg His Gln Asn Ala Gln Gly Glu
                 20                  25                  30

Gly Thr Ala Ala Asp Tyr Lys Ser Thr Gln Ser Ala Ile Asp Gln Val
             35                  40                  45

Thr Gly Lys Leu Asn Arg Leu Ile Glu Lys Thr Asn Gln Gln Phe Lys
         50                  55                  60

Leu Ile Asp Asn Glu Phe Thr Glu Val Glu Lys Gln Ile Gly Asn Val
 65                  70                  75                  80

Ile Asn Trp Thr Arg Asp Ser Met Thr Glu Val Trp Ser Tyr Asn Ala
                 85                  90                  95

Glu Leu Leu Val Ala Met Glu Asn Gln His Thr Ile Asp Leu Ala Asp
                100                 105                 110

Ser Glu Met Asn Lys Leu Tyr Glu Arg Val Lys Arg Gln Leu Arg Glu
            115                 120                 125

Asn Ala Glu Glu Asp Gly Thr Gly Cys Phe Glu Ile Phe His Lys Cys
        130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser Ser Gly Tyr Lys Asp Val Ile Leu Trp Phe Ser Phe Gly
            180                 185                 190

Ala Ser Cys Phe Ile Leu Leu Ala Ile Ala Met Gly Leu Val Phe Ile
```

```
            195                 200                 205
Cys Val Lys Asn Gly Asn Met Arg Cys Thr Ile Cys Ile
    210                 215                 220

<210> SEQ ID NO 24
<211> LENGTH: 222
<212> TYPE: PRT
<213> ORGANISM: Influenza A virus
<220> FEATURE:
<223> OTHER INFORMATION: Influenza A/H9 hemagglutinin 2

<400> SEQUENCE: 24

Gly Leu Phe Gly Ala Ile Ala Gly Phe Ile Glu Gly Gly Trp Ser Gly
 1               5                  10                  15

Leu Val Ala Gly Trp Tyr Gly Phe Gln His Ser Asn Asp Gln Gly Val
            20                  25                  30

Gly Met Ala Ala Asp Arg Asp Ser Thr Gln Lys Ala Ile Asp Lys Ile
        35                  40                  45

Thr Ser Lys Val Asn Asn Ile Val Asp Lys Met Asn Lys Gln Tyr Glu
    50                  55                  60

Ile Ile Asp His Glu Phe Ser Glu Val Glu Thr Arg Leu Asn Met Ile
65                  70                  75                  80

Asn Asn Lys Ile Asp Asp Gln Ile Gln Asp Ile Trp Ala Tyr Asn Ala
                85                  90                  95

Glu Leu Leu Val Leu Leu Glu Asn Gln Lys Thr Leu Asp Glu His Asp
            100                 105                 110

Ala Asn Val Asn Asn Leu Tyr Asn Lys Val Lys Arg Ala Leu Gly Ser
        115                 120                 125

Asn Ala Val Glu Asp Gly Lys Gly Cys Phe Glu Leu Tyr His Lys Cys
    130                 135                 140

Asp Asp Gln Cys Met Glu Thr Ile Arg Asn Gly Thr Tyr Asn Arg Arg
145                 150                 155                 160

Lys Tyr Lys Glu Glu Ser Arg Leu Glu Arg Gln Lys Ile Glu Gly Val
                165                 170                 175

Lys Leu Glu Ser Glu Gly Thr Tyr Lys Ile Leu Thr Ile Tyr Ser Thr
            180                 185                 190

Val Ala Ser Ser Leu Val Ile Ala Met Gly Phe Ala Ala Phe Leu Phe
        195                 200                 205

Trp Ala Met Ser Asn Gly Ser Cys Arg Cys Asn Ile Cys Ile
    210                 215                 220

<210> SEQ ID NO 25
<211> LENGTH: 221
<212> TYPE: PRT
<213> ORGANISM: Influenza A virus
<220> FEATURE:
<223> OTHER INFORMATION: Influenza A/H10 hemagglutinin 2

<400> SEQUENCE: 25

Gly Leu Phe Gly Ala Ile Ala Gly Phe Ile Glu Asn Gly Trp Glu Gly
 1               5                  10                  15

Met Val Asp Gly Trp Tyr Gly Phe Arg His Gln Asn Ala Gln Gly Thr
            20                  25                  30

Gly Gln Ala Ala Asp Tyr Lys Ser Thr Gln Ala Ala Ile Asp Gln Ile
        35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
```

```
                65                  70                  75                  80
Ile Asn Trp Thr Lys Asp Ser Ile Thr Asp Ile Trp Thr Tyr Asn Ala
                    85                  90                  95

Glu Leu Leu Val Ala Met Glu Asn Gln His Thr Ile Asp Met Ala Asp
                100                 105                 110

Ser Glu Met Leu Asn Leu Tyr Glu Arg Val Arg Lys Gln Leu Arg Gln
                115                 120                 125

Asn Ala Glu Glu Asp Gly Lys Gly Cys Phe Glu Ile Tyr His Thr Cys
            130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser Ser Gly Tyr Lys Asp Ile Ile Leu Trp Phe Ser Phe Gly
                180                 185                 190

Glu Ser Cys Phe Val Leu Leu Ala Val Val Met Gly Leu Val Phe Phe
            195                 200                 205

Cys Leu Lys Asn Gly Asn Met Arg Cys Thr Ile Cys Ile
    210                 215                 220

<210> SEQ ID NO 26
<211> LENGTH: 223
<212> TYPE: PRT
<213> ORGANISM: Influenza A virus
<220> FEATURE:
<223> OTHER INFORMATION: Influenza A/H13 hemagglutinin 2

<400> SEQUENCE: 26

Gly Leu Phe Gly Ala Ile Ala Gly Phe Ile Glu Gly Gly Trp Pro Gly
  1               5                  10                  15

Leu Ile Asn Gly Trp Tyr Gly Phe Gln His Gln Asn Glu Gln Gly Thr
                 20                  25                  30

Gly Ile Ala Ala Asp Lys Glu Ser Thr Gln Lys Ala Ile Asp Gln Ile
             35                  40                  45

Thr Thr Lys Ile Asn Asn Ile Ile Asp Lys Met Asn Gly Asn Tyr Asp
     50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                    85                  90                  95

Lys Leu Leu Val Leu Leu Glu Asn Asp Lys Thr Leu Asp Met His Asp
                100                 105                 110

Ala Asn Val Lys Asn Leu His Glu Gln Val Arg Arg Glu Leu Lys Asp
                115                 120                 125

Asn Ala Ile Asp Glu Gly Asn Gly Cys Phe Glu Leu Leu His Lys Cys
            130                 135                 140

Asn Asp Ser Cys Met Glu Thr Ile Arg Asn Gly Thr Tyr Asp His Thr
145                 150                 155                 160

Glu Tyr Ala Glu Glu Ser Lys Leu Lys Arg Gln Glu Ile Asp Gly Ile
                165                 170                 175

Lys Leu Lys Ser Glu Asp Asn Val Tyr Lys Ala Leu Ser Ile Tyr Ser
            180                 185                 190

Cys Ile Ala Ser Ser Val Val Leu Val Gly Leu Ile Leu Ser Phe Ile
        195                 200                 205

Met Trp Ala Cys Ser Ser Gly Asn Cys Arg Phe Asn Val Cys Ile
    210                 215                 220
```

<210> SEQ ID NO 27
<211> LENGTH: 221
<212> TYPE: PRT
<213> ORGANISM: Influenza A virus
<220> FEATURE:
<223> OTHER INFORMATION: Influenza A/H14 hemagglutinin 2

<400> SEQUENCE: 27

```
Gly Leu Phe Gly Ala Ile Ala Gly Phe Ile Glu Asn Gly Trp Gln Gly
  1               5                  10                  15

Leu Ile Asp Gly Trp Tyr Gly Phe Arg His Gln Asn Ala Glu Gly Thr
             20                  25                  30

Gly Thr Ala Ala Asp Leu Lys Ser Thr Gln Ala Ala Ile Asp Gln Ile
         35                  40                  45

Asn Gly Lys Leu Asn Arg Leu Ile Glu Lys Thr Asn Glu Lys Tyr His
 50                  55                  60

Gln Ile Glu Lys Glu Phe Glu Gln Val Glu Gly Arg Ile Gln Asp Leu
 65                  70                  75                  80

Glu Lys Tyr Val Glu Asp Thr Lys Ile Asp Leu Trp Ser Tyr Asn Ala
                 85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
            115                 120                 125

Asn Ala Glu Asp Gln Gly Asn Gly Cys Phe Glu Ile Phe His Gln Cys
130                 135                 140

Asp Asn Asn Cys Ile Glu Ser Ile Arg Asn Gly Thr Tyr Asp His Asn
145                 150                 155                 160

Ile Tyr Arg Asp Glu Ala Ile Asn Asn Arg Ile Lys Ile Asn Pro Val
                165                 170                 175

Thr Leu Thr Met Gly Tyr Lys Asp Ile Ile Leu Trp Ile Ser Phe Ser
            180                 185                 190

Met Ser Cys Phe Val Phe Val Ala Leu Ile Leu Gly Phe Val Leu Trp
            195                 200                 205

Ala Cys Gln Asn Gly Asn Ile Arg Cys Gln Ile Cys Ile
210                 215                 220
```

<210> SEQ ID NO 28
<211> LENGTH: 221
<212> TYPE: PRT
<213> ORGANISM: Influenza A virus
<220> FEATURE:
<223> OTHER INFORMATION: Influenza A/H15 hemagglutinin 2

<400> SEQUENCE: 28

```
Gly Leu Phe Gly Ala Ile Ala Gly Phe Ile Glu Asn Gly Trp Glu Gly
  1               5                  10                  15

Leu Ile Asp Gly Trp Tyr Gly Phe Arg His Gln Asn Ala Gln Gly Gln
             20                  25                  30

Gly Thr Ala Ala Asp Tyr Lys Ser Thr Gln Ala Ala Ile Asp Gln Ile
         35                  40                  45

Thr Gly Lys Leu Asn Arg Leu Ile Glu Lys Thr Asn Lys Gln Phe Glu
 50                  55                  60

Leu Ile Asp Asn Glu Phe Thr Glu Val Glu Gln Gln Ile Gly Asn Val
 65                  70                  75                  80

Ile Asn Trp Thr Arg Asp Ser Leu Thr Glu Ile Trp Ser Tyr Asn Ala
                 85                  90                  95
```

```
Glu Leu Leu Val Ala Met Glu Asn Gln His Thr Ile Asp Leu Ala Asp
            100                 105                 110

Ser Glu Met Asn Lys Leu Tyr Glu Arg Val Arg Arg Gln Leu Arg Glu
            115                 120                 125

Asn Ala Glu Glu Asp Gly Thr Gly Cys Phe Glu Ile Phe His Arg Cys
            130                 135                 140

Asp Asp Gln Cys Met Glu Ser Ile Arg Asn Asn Thr Tyr Asn His Thr
145                 150                 155                 160

Glu Tyr Arg Gln Glu Ala Leu Gln Asn Arg Ile Met Ile Asn Pro Val
            165                 170                 175

Lys Leu Ser Ser Gly Tyr Lys Asp Val Ile Leu Trp Phe Ser Phe Gly
            180                 185                 190

Ala Ser Cys Val Met Leu Leu Ala Ile Ala Met Gly Leu Ile Phe Met
            195                 200                 205

Cys Val Lys Asn Gly Asn Leu Arg Cys Thr Ile Cys Ile
            210                 215                 220

<210> SEQ ID NO 29
<211> LENGTH: 223
<212> TYPE: PRT
<213> ORGANISM: Influenza A virus
<220> FEATURE:
<223> OTHER INFORMATION: Influenza A/H16 hemagglutinin 2

<400> SEQUENCE: 29

Gly Leu Phe Gly Ala Ile Ala Gly Phe Ile Glu Gly Gly Trp Pro Gly
 1               5                  10                  15

Leu Ile Asn Gly Trp Tyr Gly Phe Gln His Gln Asn Glu Gln Gly Thr
            20                  25                  30

Gly Ile Ala Ala Asp Lys Ala Ser Thr Gln Lys Ala Ile Asp Glu Ile
            35                  40                  45

Thr Thr Lys Ile Asn Asn Ile Ile Glu Lys Met Asn Gly Asn Tyr Asp
 50                 55                  60

Ser Ile Arg Gly Glu Phe Asn Gln Val Glu Lys Arg Ile Asn Met Leu
 65                 70                  75                  80

Ala Asp Arg Val Asp Asp Ala Val Thr Asp Ile Trp Ser Tyr Asn Ala
            85                  90                  95

Lys Leu Leu Val Leu Leu Glu Asn Gly Arg Thr Leu Asp Leu His Asp
            100                 105                 110

Ala Asn Val Arg Asn Leu His Asp Gln Val Lys Arg Ile Leu Lys Ser
            115                 120                 125

Asn Ala Ile Asp Glu Gly Asp Gly Cys Phe Asn Leu Leu His Lys Cys
            130                 135                 140

Asn Asp Ser Cys Met Glu Thr Ile Arg Asn Gly Thr Tyr Asn His Glu
145                 150                 155                 160

Asp Tyr Arg Glu Glu Ser Gln Leu Lys Arg Gln Glu Ile Glu Gly Ile
            165                 170                 175

Lys Leu Lys Ser Glu Asp Asn Val Tyr Lys Val Leu Ser Ile Tyr Ser
            180                 185                 190

Cys Ile Ala Ser Ser Ile Val Leu Val Gly Leu Ile Leu Ala Phe Ile
            195                 200                 205

Met Trp Ala Cys Ser Asn Gly Asn Cys Arg Phe Asn Val Cys Ile
            210                 215                 220

<210> SEQ ID NO 30
<211> LENGTH: 223
```

```
<212> TYPE: PRT
<213> ORGANISM: Influenza B virus
<220> FEATURE:
<223> OTHER INFORMATION: Influenza B hemagglutinin 2

<400> SEQUENCE: 30

Gly Phe Phe Gly Ala Ile Ala Gly Phe Leu Glu Gly Gly Trp Glu Gly
 1               5                  10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Asp Ile Gly Asn Gly Cys Phe Glu Thr Lys His Lys Cys
    130                 135                 140

Asn Gln Thr Cys Leu Asp Arg Ile Ala Ala Gly Thr Phe Asn Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Ile
        195                 200                 205

Val Tyr Met Val Ser Arg Asp Asn Val Ser Cys Ser Ile Cys Leu
    210                 215                 220

<210> SEQ ID NO 31
<211> LENGTH: 7
<212> TYPE: PRT
<213> ORGANISM: Influenza A Virus
<220> FEATURE:
<223> OTHER INFORMATION: Residues 5-11 of hemagglutinin 2 from
      influenza A subtypes: H1-H7, H9, H10, and H13-H16

<400> SEQUENCE: 31

Ala Ile Ala Gly Phe Ile Glu
 1               5
```